(12) United States Patent
Vaillancourt et al.

(10) Patent No.: US 6,727,248 B2
(45) Date of Patent: *Apr. 27, 2004

(54) SUBSTITUTED QUINOLINECARBOXAMIDES AS ANTIVIRAL AGENTS

(75) Inventors: Valerie A. Vaillancourt, Kalamazoo, MI (US); Audris Huang, Irvine, CA (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/350,248

(22) Filed: Jan. 23, 2003

(65) Prior Publication Data

US 2003/0149035 A1 Aug. 7, 2003

Related U.S. Application Data

(62) Division of application No. 10/084,015, filed on Feb. 27, 2002, now Pat. No. 6,544,990.
(60) Provisional application No. 60/272,607, filed on Mar. 1, 2001.

(51) Int. Cl.[7] .................. A61K 31/5375; C07D 413/00; A61P 31/12
(52) U.S. Cl. ..................... 514/235.2; 544/128
(58) Field of Search ........................ 544/128; 514/235.2

(56) References Cited

U.S. PATENT DOCUMENTS

| 5,891,878 A | 4/1999 | Beasley et al. .............. 514/247 |
| 6,544,990 B2 * | 4/2003 | Vaillancourt et al. .... 514/235.2 |

FOREIGN PATENT DOCUMENTS

| WO | WO 99/32450 | 7/1999 | ......... C07D/215/56 |
| WO | WO 00/40561 | 7/2000 | ......... C07D/215/16 |
| WO | WO 00/40563 | 7/2000 | ......... C07D/215/56 |
| WO | WO 02/06513 | 1/2002 | ............ C12Q/1/00 |

* cited by examiner

Primary Examiner—Joseph K. McKane
Assistant Examiner—Robert Shiao
(74) Attorney, Agent, or Firm—Lucy X. Yang

(57) ABSTRACT

The present invention discloses disubstiuted 4-oxo-1,4-dihydro-3-quinolinecarboxamide derivatives. The compounds are useful as antiviral agents, in particular, as agents against viruses of the herpes family.

9 Claims, No Drawings

SUBSTITUTED QUINOLINECARBOXAMIDES AS ANTIVIRAL AGENTS

This application is a divisional of U.S. Ser. No. 10/084,015, filed Feb. 27, 2002 now U.S. Pat. No. 6,544,990 which claims the benefit of U.S. Serial No. 60/272,607, filed Mar. 1, 2001, under 35 USC 119(e)(i), incorporated herein, by reference in their entirety.

FIELD OF THE INVENTION

The present invention discloses disubstiuted 4-oxo-1,4-dihydro-3-quinolinecarboxamide derivatives, and more specifically, provides compounds of formula (I) described herein below. These compounds are useful as antiviral agents, in particular, as agents against viruses of the herpes family.

BACKGROUND OF THE INVENTION

The herpesviruses comprise a large family of double stranded DNA viruses. They are also a source of the most common viral illnesses in man. Eight of the herpes viruses, herpes simplex virus types 1 and 2 (HSV-1 and HSV-2), varicella zoster virus (VZV), human cytomegalovirus (HCMV), epstein-Barr virus (EBV), and human herpes viruses 6, 7, and 8 (HHV-6, HHV-7, and HHV-8), have been shown to infect humans.

HSV-1 and HSV-2 cause herpetic lesions on the lips and genitals, respectively. They also occasionally cause infections of the eye and encephalitis. HCMV causes birth defects in infants and a variety of diseases in immunocompromised patients such as retinitis, pneumonia, and gastrointestinal disease. VZV is the causitive agent of chicken pox and shingles. EBV causes infectious mononucleosis. It can also cause lymphomas in immunocompromised patients and has been associated with Burkitt's lymphoma, nasopharyngeal carcinoma, and Hodgkins disease. HHV-6 is the causative agent of roseola and may be associated with multiple sclerosis and chronic fatigue syndrome. HHV-7 disease association is unclear, but it may be involved in some cases of roseola. HHV-8 has been associated with Karposi's sarcoma, body cavity based lymphomas, and multiple myeloma.

Due to the selective substitutents, Y and Z, on the quinoline ring, and the unique position of the X substitutent on the N-phenylmethyl of formula I described herein below, compounds of the present invention demonstrate unexpected activity against the above reference herpesviral infections, particularly, human cytomegaloviral infection.

INFORMATION DISCLOSURE

U.S. Pat. No. 5,891,878 discloses the use of compounds of the following structure for the treatment of a disease state capable of being modulated by inhibition of production of phosphodiesterase IV or tumor necrosis factor,

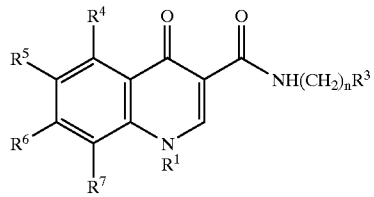

PCT publication, WO99/32450 discloses compounds of the structure below

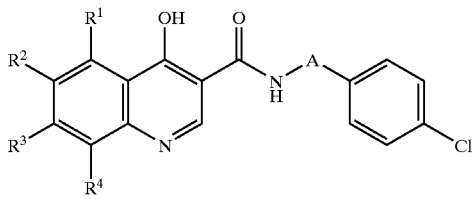

which are useful as antiviral agents.

PCT publication, WO00/40561 discloses the quinolinecarboxamide structure below as antiviral agents:

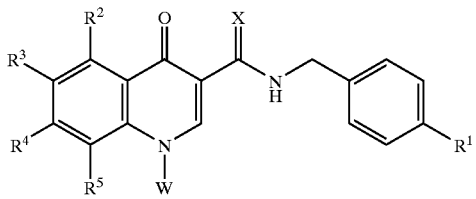

PCT publication, WO00/40563 discloses the 4-oxo-1,4-dihydro-3-uqinolinecarboxamide structure below as antiviral agents:

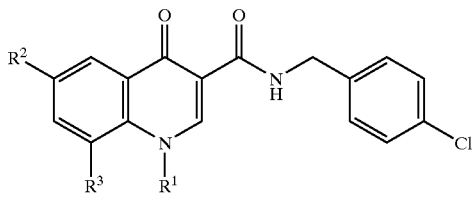

SUMMARY OF THE INVENTION

The present invention provides a compound of formula I

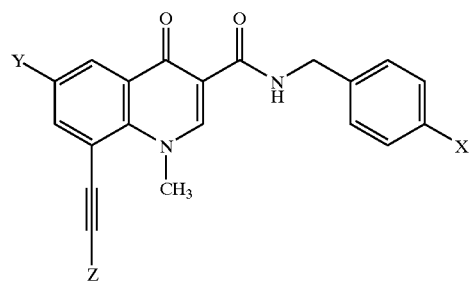

or a pharmaceutically acceptable salt thereof wherein
X is Cl, Br, CN, $NO_2$, or F;
Y is morpholinylmethyl, tetrahydro-2H-pyranylmethyl, hydroxypropynyl, or hydroxypropyl;

Z is het[1], or $C_{1-7}$alkyl optionally substituted with at least one halo, $NR_1R_2$, $OR^3$, or het[2];

$R^1$ and $R^2$ are independently H, $C_{1-7}$alkyl, or $C_{2-7}$alkyl substituted with at least one OH;

$R^3$ is H, or $C_{1-7}$alkyl;

het[1] is a five-(5), or six-(6) membered saturated or unsaturated heterocyclic ring bonded via a carbon atom having 1, 2, or 3 heteroatoms selected from the group consisting of oxygen, sulfur, or nitrogen, wherein the het is optionally fused to a benzene ring, and optionally substituted with one or more substituents selected from the group consisting of halo, $OR^3$, CN, phenyl, $C_2R^3$, $CF_3$, or $C_{1-6}$ alkyl which may be further substituted by one to three $SR^3$, $NR^3R^3$, $OR^3$, or $CO_2R^3$ groups; and het[2] is a five-(5), or six-(6) membered saturated or unsaturated heterocyclic ring having 1, 2, or 3 heteroatoms selected from the group consisting of oxygen, sulfur, or nitrogen, wherein het is optionally fused to a benzene ring, and optionally substituted with one or more substituents selected from the group consisting of halo, $OR^3$, CN, phenyl, $CO_2R^3$, $CF_3$, oxo, oxime, or $C_{1-6}$ alkyl which may be further substituted by one to three $SR^3$, $NR^3R^3$, $OR^3$, or $CO_2R^3$ groups.

In another aspect, the present invention also provides:

A pharmaceutical composition which comprises a pharmaceutically acceptable carrier and an effective amount of a compound of formula I, a method of treating and preventing herpesviral infections in a mammal, including human, and a method for inhibiting a viral DNA polymerase, comprising contacting the polymerase with an effective inhibitory amount of a compound of claim 1, or a pharmaceutically acceptable salt thereof, a compound of formula I or a pharmaceutically acceptable salt thereof for use in medical treatment or prevention of a herpesviral infection in a mammal.

The invention also provides novel intermediates and processes disclosed herein that are useful for preparing compounds of formula I.

DETAILED DESCRIPTION OF THE INVENTION

For the purpose of the present invention, the carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, ($C_{1-7}$)alkyl refers to alkyl of one to seven carbon atoms, inclusive, or methyl, ethyl, propyl, butyl, pentyl, hexyl, and heptyl, straight and branched forms thereof.

The term "het[1]" is a five-(5), or six-(6) membered saturated or unsaturated heterocyclic ring bonded via a carbon atom having 1, 2, or 3 heteroatoms selected from the group consisting of oxygen, sulfur, or nitrogen, wherein the het is optionally fused to a benzene ring, and optionally substituted with one or more substituents selected from the group consisting of halo, OH, CN, phenyl, $CO_2R^3$, $CF_3$, $OC_{1-6}$alkyl, or $C_{1-6}$ alkyl which may be further substituted by one to three $SR^3$, $NR^3R^3$, $OR^3$, or $CO_2R^3$ groups.

The term "het[2]" is a five-(5), or six-(6) membered saturated or unsaturated heterocyclic ring having 1, 2, or 3 heteroatoms selected from the group consisting of oxygen, sulfur, or nitrogen, wherein het is optionally fused to a benzene ring, and optionally substituted with one or more substituents selected from the group consisting of halo, OH, CN, phenyl, $CO_2R^3$, $CF_3$, $OC_{1-6}$alkyl, oxo, oxime, or $C_{1-6}$alkyl which may be further substituted by one to three $SR^3$, $NR^3R^3$, $OR^3$, or $CO_2R^3$ groups. The preferred substitutent is oxo or hydroxy.

When a het contains a sulfur atom, the sulfur atom may be mono- or di-oxidized.

Examples of "het[1]" include, but not limit to, pyridine, imidazole, thiazole, oxazole, thiadiazole, oxadiazole, imidazoline, pyrimidine, pyrazine, or indole.

Examples "het[2]" include, but not limit to, imidazolidine, imidazoline, pyrazolidine, pyrazoline, dioxolane, imidazole, oxathiolane, oxazolidine, pyrrolidine, pyrroline, piperidine, piperazine, morpholine, thiomorpholine, isochroman, chroman, indoline, or isoindoline.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, tautomeric, or stereoisomeric form, or mixture thereof, of a compound of the invention, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine antiviral activity using the standard tests described herein, or using other similar tests which are well known in the art.

The compounds of the present invention are generally named according to the IUPAC or CAS nomenclature system. "Pharmaceutically acceptable salts" refers to those salts which possess the biological effectiveness and properties of the parent compound and which are not biologically or otherwise undesirable.

Mammal refers to human and animals.

"Optionally" or "may be" means that the subsequently described event or circumstance may, but need not, occur, and that the description includes instances where the event or circumstance occurs and instances in which it does not.

A "pharmaceutically acceptable carrier" means a carrier that is useful in preparing a pharmaceutical composition that is generally safe, non-toxic and neither biologically nor otherwise undesirable, and includes a carrier that is acceptable for veterinary use as well as human pharmaceutical use. "A pharmaceutically acceptable carrier" as used in the specification and claims includes both one and more than one such carrier.

Specifically, X is chloro.

Specifically, Z is C1–7alkyl optionally substituted with one or two OR3.

Specifically, Z is methyl, ethyl or propyl substituted with one or two OH.

Specifically, Z is methyl, ethyl or propyl substituted with NR1 R2 wherein R1 and R2 are independently H, C1–4alkyl, or C2–6alkyl substituted with one or two OH;

Specifically, Z is methyl or ethyl substituted with N(CH3)2.

Specifically, Z is methyl or ethyl substituted with het2.

Specifically, het1 is pyridine, imidazole, thiazole, oxazole, thiadiazole, oxadiazole, imidazole, pyrimidine, pyrazine, or indole.

Specifically, het2 is 2-oxo-1,3-oxazolidin-4-yl.

Specifically, het2 is 1,1-dioxido-4-thiomorpholinyl.

Specifically, Y is 4-morpholinylmethyl.

Specifically, Y is tetrahydro-2H-pyran-4-ylmethyl.

Specifically, Y is 3-hydroxy-1-propynyl, or 3-hydroxypropyl.

Examples of the present invention are:
(1) N-(4-chlorobenzyl)-8-(3-hydroxy-1-propynyl)-1-methyl-4-oxo-6-(tetrahydro-2H-pyran-4-ylmethyl)-1,4-dihydro-3-quinolinecarboxamide,
(2) N-(4-chlorobenzyl)-8-(4-hydroxy-1-butynyl)-1-methyl-4-oxo-6-(tetrahydro-2H-pyran-4-ylmethyl)-1,4-dihydro-3-quinolinecarboxamide,
(3) N-(4-chlorobenzyl)-8-[3-(dimethylamino)-1-propynyl]-1-methyl-4-oxo-6-(tetrahydro-2H-pyran-4-ylmethyl)-1,4-dihydro-3-quinolinecarboxamide,
(4) N-(4-chlorobenzyl)-8-(3-hydroxy-1-propynyl)-1-methyl-6-(4-morpholinylmethyl)-4-oxo-1,4-dihydro-3-quinolinecarboxamide,
(5) N-(4-chlorobenzyl)-8-[3-(dimethylamino)-1-propynyl]-1-methyl-6-(4-morpholinylmethyl)-4-oxo-1,4-dihydro-3-quinolinecarboxamide,
(6) N-(4-chlorobenzyl)-8-(4-hydroxy-1-butynyl)-1-methyl-6-(4-morpholinylmethyl)-4-oxo-1,4-dihydro-3-quinolinecarboxamide,
(7) N-(4-chlorobenzyl)-8-[(3S)-3-hydroxy-1-butynyl]-1-methyl-6-(4-morpholinylmethyl)-4-oxo-1,4-dihydro-3-quinolinecarboxamide,
(8) N-(4-chlorobenzyl)-8-[(3R)-3-hydroxy-1-butynyl]-1-methyl-6-(4-morpholinylmethyl)-4-oxo-1,4-dihydro-3-quinolinecarboxamide,
(9) N-(4-chlorobenzyl)-1-methyl-6-(4-morpholinylmethyl)-4-oxo-8-{4-[(4R)-2-oxo-1,3-oxazolidin-4-yl]-1-butynyl}-1,4-dihydro-3-quinolinecarboxamide,
(10) N-(4-chlorobenzyl)-8-(5-hydroxy-1-pentynyl)-1-methyl-6-(4-morpholinylmethyl)-4-oxo-1,4-dihydro-3-quinolinecarboxamide,
(11) N-(4-chlorobenzyl)-8-[3-(1,1-dioxido-4-thiomorpholinyl)-1-propynyl]-1-methyl-6-(4-morpholinylmethyl)-4-oxo-1,4-dihydro-3-quinolinecarboxamide,
(12) N-(4-chlorobenzyl)-1-methyl-8-[3-(5-methyl-1H-imidazol-1-yl)prop-1-ynyl]-6-(morpholin-4-ylmethyl)-4-oxo-1,4-dihydroquinoline-3-carboxamide,
(13) N-(4-chlorobenzyl)-8-[3-(4,5-dichloro-1H-imidazol-1-yl)prop-1-ynyl]-1-methyl-6-(morpholin-4-ylmethyl)-4-oxo-1,4-dihydroquinoline-3-carboxamide,
(14) N-(4-chlorobenzyl)-8-(3-fluoroprop-1-ynyl)-1-methyl-6-(morpholin-4-ylmethyl)-4-oxo-1,4-dihydroquinoline-3-carboxamide,
(15) N-(4-chlorobenzyl)-1-methyl-6-(morpholin-4-ylmethyl)-4-oxo-8-(pyridin-2-ylethynyl)-1,4-dihydroquinoline-3-carboxamide,
(16) N-(4-chlorobenzyl)-1-methyl-6-(morpholin-4-ylmethyl)-4-oxo-8-(pyridin-3-ylethynyl)-1,4-dihydroquinoline-3-carboxamide,
(17) N-(4-chlorobenzyl)-1-methyl-6-(morpholin-4-ylmethyl)-4-oxo-8-(pyridin-4-ylethynyl)-1,4-dihydroquinoline-3-carboxamide,
(18) N-(4-chlorobenzyl)-8-(4-hydroxypent-1-ynyl)-1-methyl-6-(morpholin-4-ylmethyl)-4-oxo-1,4-dihydroquinoline-3-carboxamide,
(19) N-(4-chlorobenzyl)-8-[3-(4-hydroxypiperidin-1-yl)prop-1-ynyl]-1-methyl-6-(morpholin-4-ylmethyl)-4-oxo-1,4-dihydroquinoline-3-carboxamide,
(20) N-(4-chlorobenzyl)-8-[3-(3-hydroxypyrrolidin-1-yl)prop-1-ynyl]-1-methyl-6-(morpholin-4-ylmethyl)-4-oxo-1,4-dihydroquinoline-3-carboxamide,
(21) N-(4-chlorobenzyl)-8-{3-[(2,3-dihydroxypropyl)(methyl)amino]prop-1-ynyl}-1-methyl-6-(morpholin-4-ylmethyl)-4-oxo-1,4-dihydroquinoline-3-carboxamide,
(22) N-(4-chlorobenzyl)-8-{3-[(2-hydroxyethyl)(methyl)amino]prop-1-ynyl}-1-methyl-6-(morpholin-4-ylmethyl)-4-oxo-1,4-dihydroquinoline-3-carboxamide,
(23) N-(4-chlorobenzyl)-8-[3-(1H-imidazol-1-yl)prop-1-ynyl]-1-methyl-6-(morpholin-4-ylmethyl)-4-oxo-1,4-dihydroquinoline-3-carboxamide,
(24) N-(4-chlorobenzyl)-8-[5-hydroxy-4-(hydroxymethyl)pent-1-ynyl]-1-methyl-6-(morpholin-4-ylmethyl)-4-oxo-1,4-dihydroquinoline-3-carboxamide,
(25) N-(4-chlorobenzyl)-8-{3-[3-(hydroxymethyl)piperidin-1-yl]prop-1-ynyl}-1-methyl-6-(morpholin-4-ylmethyl)-4-oxo-1,4-dihydroquinoline-3-carboxamide,
(26) N-(4-chlorobenzyl)-8-{3-[4-(2-hydroxyethyl)piperazin-1-yl]prop-1-ynyl}-1-methyl-6-(morpholin-4-ylmethyl)-4-oxo-1,4-dihydroquinoline-3-carboxamide,
(27) N-(4-chlorobenzyl)-8-{3-[(2S)-2-(hydroxymethyl)pyrrolidin-1-yl]prop-1-ynyl}-1-methyl-6-(morpholin-4-ylmethyl)-4-oxo-1,4-dihydroquinoline-3-carboxamide,
(28) N-(4-chlorobenzyl)-8-[3-(3-hydroxypiperidin-1-yl)prop-1-ynyl]-1-methyl-6-(morpholin-4-ylmethyl)-4-oxo-1,4-dihydroquinoline-3-carboxamide,
(29) N-(4-chlorobenzyl)-8-{3-[(2R)-2-(hydroxymethyl)pyrrolidin-1-yl]prop-1-ynyl}-1-methyl-6-(morpholin-4-ylmethyl)-4-oxo-1,4-dihydroquinoline-3-carboxamide,
(30) N-(4-chlorobenzyl)-8-{3-[2-(2-hydroxyethyl)piperidin-1-yl]prop-1-ynyl}-1-methyl-6-(morpholin-4-ylmethyl)-4-oxo-1,4-dihydroquinoline-3-carboxamide,
(31) 8-{3-[butyl(2-hydroxyethyl)amino]prop-1-ynyl}-N-(4-chlorobenzyl)-1-methyl-6-(morpholin-4-ylmethyl)-4-oxo-1,4-dihydroquinoline-3-carboxamide.

The examples of the preferred compounds of the present invention are:
(1) N-(4-chlorobenzyl)-8-(4-hydroxybut-1-ynyl)-1-methyl-6-(morpholin-4-ylmethyl)-4-oxo-1,4-dihydroquinoline-3-carboxamide,
(2) N-(4-chlorobenzyl)-8-[3-(1,1-dioxidothiomorpholin-4-yl)prop-1-ynyl]-1-methyl-6-(morpholin-4-ylmethyl)-4-oxo-1,4-dihydroquinoline-3-carboxamide,
(3) N-(4-chlorobenzyl)-1-methyl-8-[3-(5-methyl-1H-imidazol-1-yl)prop-1-ynyl]-6-(morpholin-4-ylmethyl)-4-oxo-1,4-dihydroquinoline-3-carboxamide,
(4) N-(4-chlorobenzyl)-8-(4-hydroxypent-1-ynyl)-1-methyl-6-(morpholin-4-ylmethyl)-4-oxo-1,4-dihydroquinoline-3-carboxamide,
(5) N-(4-chlorobenzyl)-8-(4-hydroxybut-1-ynyl)-1-methyl-4-oxo-6-(tetrahydro-2H-pyran-4-ylmethyl)-1,4-dihydroquinoline-3-carboxamide,
(6) N-(4-chlorobenzyl)-8-[3-(dimethylamino)prop-1-ynyl]-1-methyl-4-oxo-6-(tetrahydro-2H-pyran-4-ylmethyl)-1,4-dihydroquinoline-3-carboxamide,
(7) N-(4-chlorobenzyl)-8-[(3R)-3-hydroxybut-1-ynyl]-1-methyl-6-(morpholin-4-ylmethyl)-4-oxo-1,4-dihydroquinoline-3-carboxamide, (8) N-(4-chlorobenzyl)-8-[3-(dimethylamino)prop-1-ynyl]-1-methyl-6-(morpholin-4-ylmethyl)-4-oxo-1,4-dihydroquinoline-3-carboxamide, (9) N-(4-chlorobenzyl)-8-[(3S)-3-hydroxybut-1-ynyl]-1-methyl-6-(morpholin-4-ylmethyl)-4-oxo-1,4-dihydroquinoline-3-carboxamide,

(10) N-(4-chlorobenzyl)-8-[5-hydroxy-4-(hydroxymethyl)pent-1-ynyl]-1-methyl-6-(morpholin-4-ylmethyl)-4-oxo-1,4-dihydroquinoline-3-carboxamide,

(11) N-(4-chlorobenzyl)-8-{3-[4-(2-hydroxyethyl)piperazin-1-yl]prop-1-ynyl}-1-methyl-6-(morpholin-4-ylmethyl)-4-oxo-1,4-dihydroquinoline-3-carboxamide,

(12) N-(4-chlorobenzyl)-8-[3-(1H-imidazol-1-yl)prop-1-ynyl]-1-methyl-6-(morpholin-4-ylmethyl)-4-oxo-1,4-dihydroquinoline-3-carboxamide,

(13) N-(4-chlorobenzyl)-1-methyl-6-(morpholin-4-ylmethyl)-4-oxo-8-(pyridin-3-ylethynyl)-1,4-dihydroquinoline-3-carboxamide,

(14) N-(4-chlorobenzyl)-8-[3-(4,5-dichloro-1H-imidazol-1-yl)prop-1-ynyl]-1-methyl-6-(morpholin-4-ylmethyl)-4-oxo-1,4-dihydroquinoline-3-carboxamide,

(15) N-(4-chlorobenzyl)-8-(5-hydroxypent-1-ynyl)-1-methyl-6-(morpholin-4-ylmethyl)-4-oxo-1,4-dihydroquinoline-3-carboxamide,

(16) N-(4-chlorobenzyl)-8-(3-hydroxyprop-1-ynyl)-1-methyl-4-oxo-6-(tetrahydro-2H-pyran-4-ylmethyl)-1,4-dihydroquinoline-3-carboxamide,

(17) N-(4-chlorobenzyl)-8-{3-[2-(2-hydroxyethyl)piperidin-1-yl]prop-1-ynyl}-1-methyl-6-(morpholin-4-ylmethyl)-4-oxo-1,4-dihydroquinoline-3-carboxamide,

(18) N-(4-chlorobenzyl)-8-{3-[(2R)-2-(hydroxymethyl)pyrrolidin-1-yl]prop-1-ynyl}-1-methyl-6-(morpholin-4-ylmethyl)-4-oxo-1,4-dihydroquinoline-3-carboxamide,

(19) N-(4-chlorobenzyl)-8-{3-[3-(hydroxymethyl)piperidin-1-yl]prop-1-ynyl}-1-methyl-6-(morpholin-4-ylmethyl)-4-oxo-1,4-dihydroquinoline-3-carboxamide,

(20) N-(4-chlorobenzyl)-8-{3-[(2,3-dihydroxypropyl)(methyl)amino]prop-1-ynyl}-1-methyl-6-(morpholin-4-ylmethyl)-4-oxo-1,4-dihydroquinoline-3-carboxamide,

(21) N-(4-chlorobenzyl)-1-methyl-6-(morpholin-4-ylmethyl)-4-oxo-8-(pyridin-4-ylethynyl)-1,4-dihydroquinoline-3-carboxamide,

(22) N-(4-chlorobenzyl)-1-methyl-6-(morpholin-4-ylmethyl)-4-oxo-8-{4-[(4R)-2-oxo-1,3-oxazolidin-4-yl]but-1-ynyl}-1,4-dihydroquinoline-3-carboxamide,

(23) N-(4-chlorobenzyl)-8-[3-(3-hydroxypyrrolidin-1-yl)prop-1-ynyl]-1-methyl-6-(morpholin-4-ylmethyl)-4-oxo-1,4-dihydroquinoline-3-carboxamide,

(24) N-(4-chlorobenzyl)-8-{3-[(2S)-2-(hydroxymethyl)pyrrolidin-1-yl]prop-1-ynyl}-1-methyl-6-(morpholin-4-ylmethyl)-4-oxo-1,4-dihydroquinoline-3-carboxamide,

(25) N-(4-chlorobenzyl)-8-(3-fluoroprop-1-ynyl)-1-methyl-6-(morpholin-4-ylmethyl)-4-oxo-1,4-dihydroquinoline-3-carboxamide,

(26) N-(4-chlorobenzyl)-1-methyl-6-(morpholin-4-ylmethyl)-4-oxo-8-(pyridin-2-ylethynyl)-1,4-dihydroquinoline-3-carboxamide,

(27) N-(4-chlorobenzyl)-8-[3-(3-hydroxypiperidin-1-yl)prop-1-ynyl]-1-methyl-6-(morpholin-4-ylmethyl)-4-oxo-1,4-dihydroquinoline-3-carboxamide.

The following Schemes A–G describe the preparation of the compounds of formula I of the present invention. All of the starting materials are prepared by procedures described in these schemes, by procedures well known to one of ordinary skill in organic chemistry or can be obtained commercially. All of the final compounds of the present invention are prepared by procedures described in these schemes or by procedures analogous thereto, which would be well known to one of ordinary skill in organic chemistry. All of the variables used in the schemes are as defined below or as in the claims.

Scheme A illustrates the preparation of the precursors to compounds of formula I wherein Y is tetrahydropyranylmethyl.

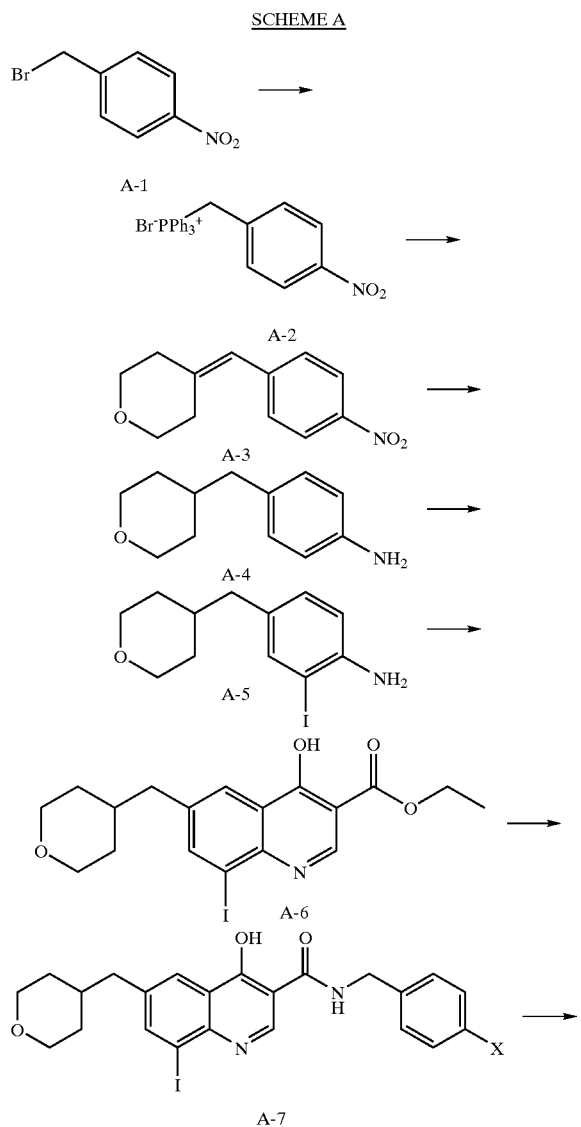

SCHEME A

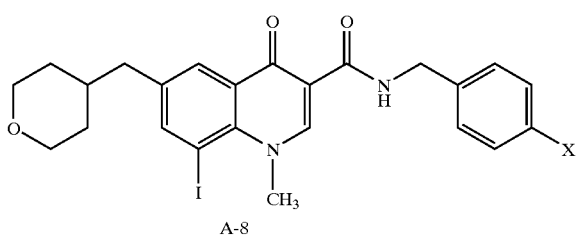

A-8

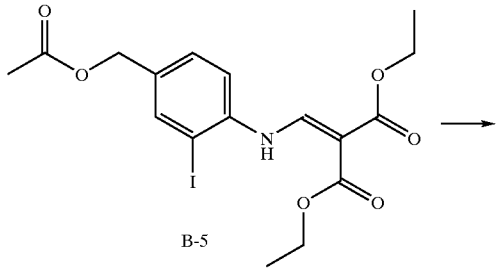

B-5

As shown in Scheme A, treatment of 4-nitrobenzylbromide with triphenylphosphine provides the phosphonium salt A-2 which undergoes a Wittig reaction with tetrahydrapyran-4-one to give the nitrobenzylidine A-3. Reduction provides the tetrahydropyranylmethylaniline A-4 which can be condensed with diethyl ethoxymethylenemalonate and cyclized to give the quinoline A-6. Treatment with an amine such as 4-chlorobenzylamine at elevated temperatures gives the corresponding amide A-7. Alkylation of the N-1 nitrogen by treatment with potassium or cesium carbonate and an alkylating agent such as methyl iodide provides the N-methyl-oxo-dihydroquinoline A-8.

Scheme B illustrates the preparation of the precursors to compounds of formula I wherein Y is morpholinylmethyl.

SCHEME B

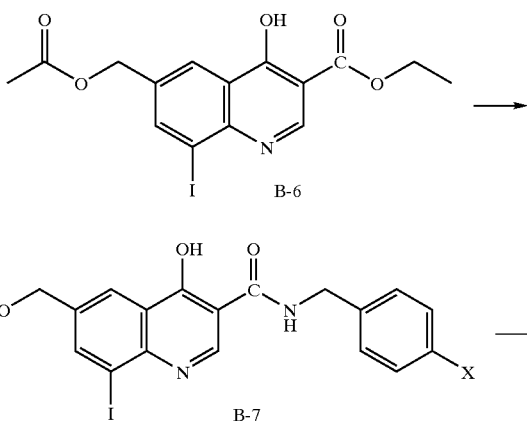

B-1

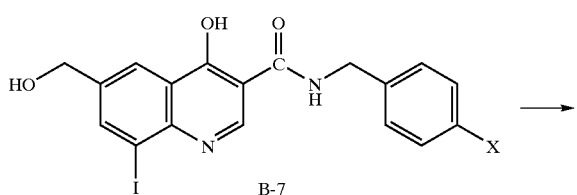

B-6

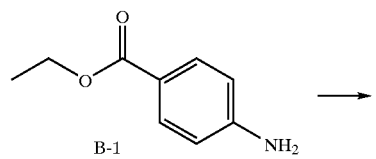

B-2

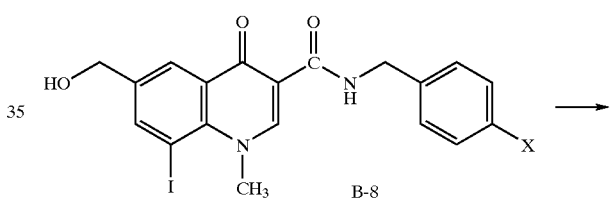

B-7

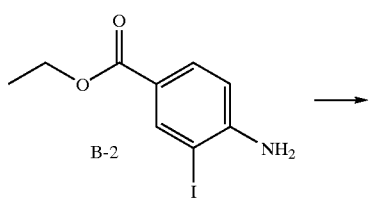

B-3

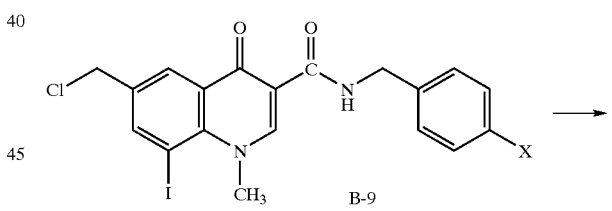

B-8

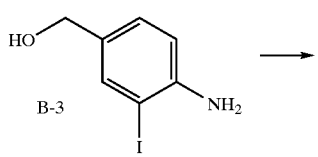

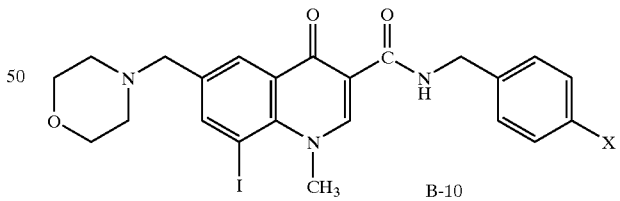

B-9

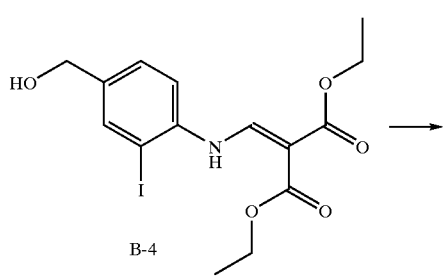

B-4

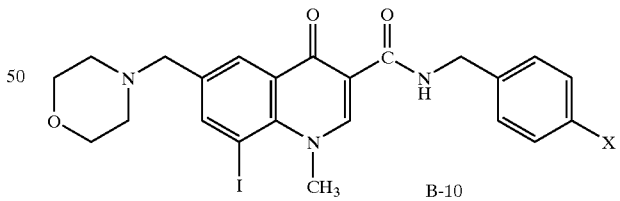

B-10

As shown in Scheme B, iodination of ethyl aminobenzoate with N-iodosuccinimide followed by reduction of the ester with diisobutylaluminium hydride or superhydride provides the hydroxymethyl aniline B-3. Condensation with diethyl ethoxymethylenemalonate followed by protection of the hydroxymethyl group as the corresponding acetate and thermal cyclization provides the quinoline carboxylic ester B-6. Treatment with an amine such as 4-chlorobenzyl amine at elevated temperature results in deprotection of the acetate and conversion to the corresponding amide B-7. Alkylation of the N-1 nitrogen by treatment with an alkylating agent such as methyl iodide in the presence of a base such as potassium or cesium carbonate gives the 4-oxo-dihydroquinoline B-8. Conversion of the hydroxymethyl group to a chloromethyl group by treatment with MsCl in collidine followed by displacement of the chloride with an amine (such as morpholine) provides the morpholinylmethyl quinolone B-10.

Scheme C illustrates the preparation of the precursors to compounds of formula I wherein Y is 3-hydroxypropynyl.

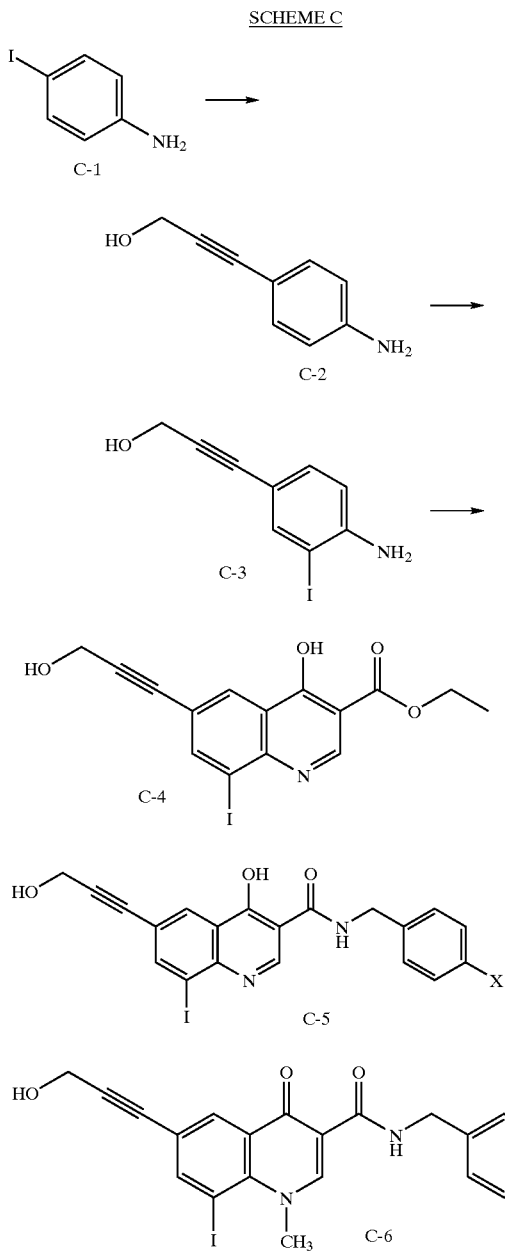

As shown in Scheme C, palladium-catalyzed coupling of the iodoaniline C-1 with an acetylene such as propargyl alcohol followed by iodination with an iodinating agent such as ICl provides the iodoaniline C-3. Condensation with diethyl ethoxymethylenemalonate and cyclization either under thermal conditions provides the quinoline carboxylic ester C-4. Treatment of the ester with an amine such as 4-chlorobenzylamine at elevated temperature and subsequent alkylation of the N-1 nitrogen as in the previous charts provides the 3-hydroxypropynyl-4-oxo-dihydroquinoline C-6.

Scheme D illustrates the preparation of the precursors to compounds of formula I wherein Y is 3-hydroxypropyl.

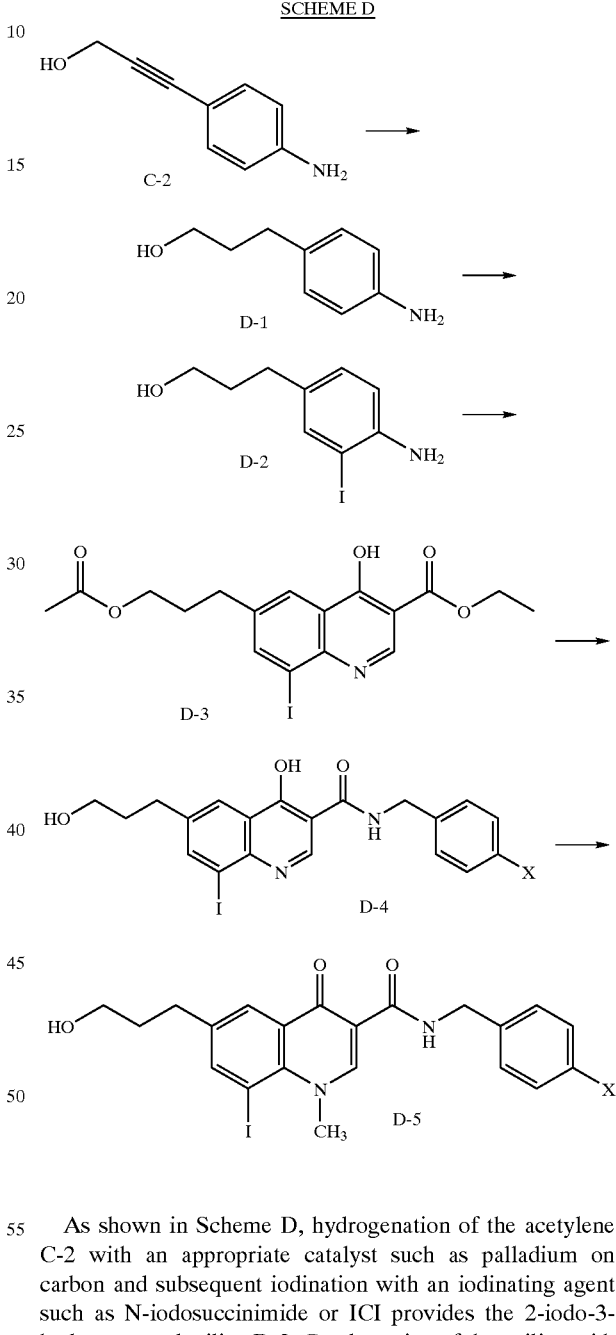

As shown in Scheme D, hydrogenation of the acetylene C-2 with an appropriate catalyst such as palladium on carbon and subsequent iodination with an iodinating agent such as N-iodosuccinimide or ICl provides the 2-iodo-3-hydroxypropylaniline D-2. Condensation of the aniline with diethyl ethoxymethylenemalonate, protection of the alcohol as the corresponding acetate and cyclization under thermal conditions provides the quinoline carboxylic ester D-3. Treatment of the ester with an amine such as 4-chlorobenzylamine results in both conversion to the corresponding amide and deprotection of the acetate group to give D-4. Alkylation of the N-1 nitrogen by treatment with an alkylating agent such as methyl iodide in the presence of a base such as potassium or cesium carbonate provides the 6-(3-hydroxypropyl)-8-iodo-4-oxo-dihydroquinoline D-5.

Alternatively, many of the above quinolines can be prepared starting with anilines which already incorporate the N-1 alkyl group as shown in Scheme E. In these cases, conversion of the aniline to the corresponding quinoline E-2 can be accomplished by condensation with diethyl ethoxymethylenemalonate and subsequent cyclization by treatment with Eaton's reagent. Conversion to the corresponding amide can be accomplished in several ways including treatment of the ester with an appropriate amine such as 4-chlorobenzylamine at elevated temperatures or saponification to the acid, activation of the acid and coupling with the desired amine. The requisite N-alkyl anilines can be prepared in an analogous manner as the anilines described above.

The precursors described above can undergo Sonogashira couplings (PdCl2(PPh3)2, CuI, Et2NH) with substituted acetylenes to provide the desired compounds as shown in Scheme F.

SCHEME F

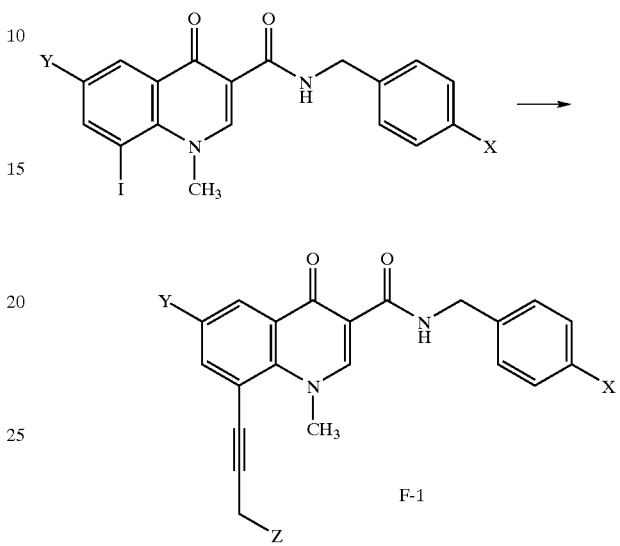

SCHEME E

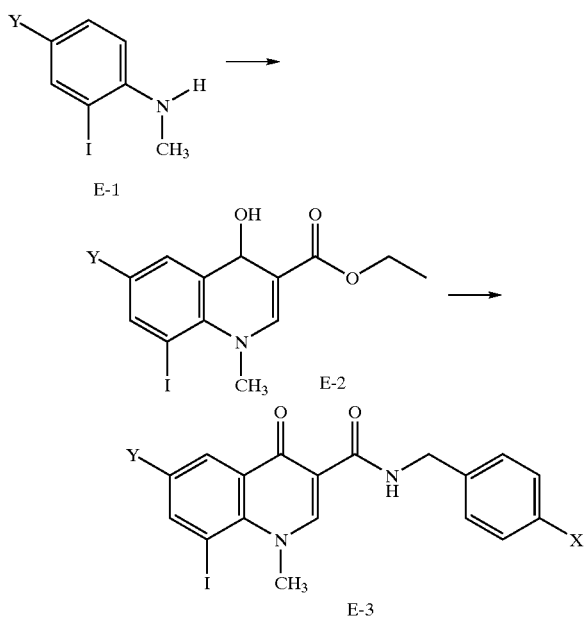

As shown in Scheme G, the starting material G-0, whose preparation is described Scheme as B-10 (wherein X is chloro), is reacted with propargyl alcohol under palladium catalyzed conditions to afford the compound of formula G-1 [N-(4-chlorobenzyl)-8-(3-hydroxy-1-propynyl)-1-methyl-6-(4-morpholinylmethyl)-4-oxo-1,4-dihydro-3-quinolinecarboxamide]. The alcohol of compound G-1 is converted to a leaving group and is displaced by various het to afford compounds of formula G-2. Alternatively, the alcohol of the compound of formula G-1 is converted to a leaving group and is reacted with amines to afford compounds of formula G-3.

SCHEME G

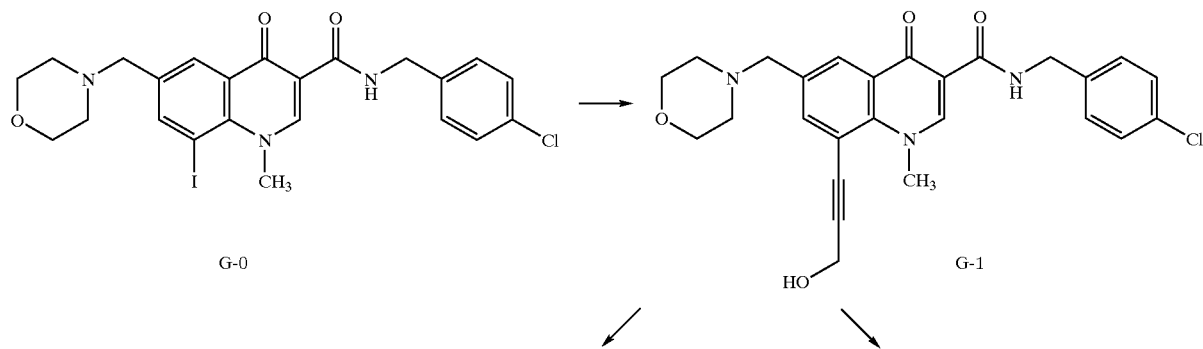

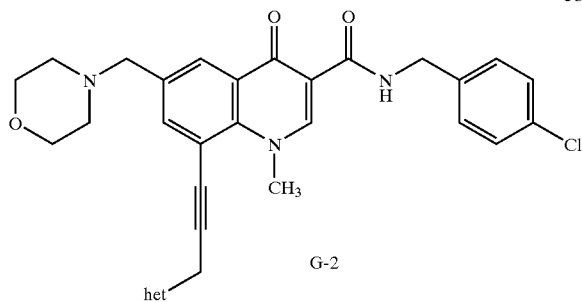

G-2

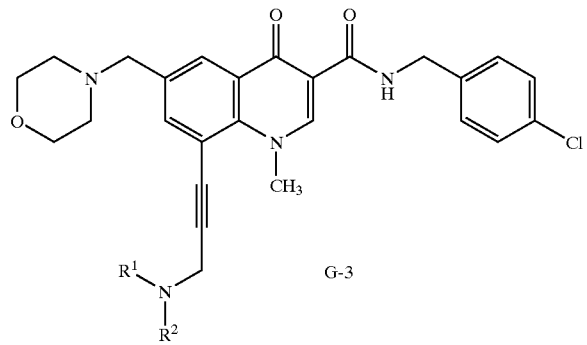

G-3

It will be apparent to those skilled in the art that the described synthetic procedures are merely representative in nature and alternative synthetic processes are known to one of ordinary skill in organic chemistry.

The compounds of the present invention and pharmaceutically acceptable salts thereof are useful as antiviral agents. Thus, these compounds are useful to combat to viral infections in mammals. Specifically, these compounds have antiviral activity against the herpes virus, cytomegalovirus (CMV). These compounds are also active against other herpes viruses, such as the varicella zoster virus, the Epstein-Barr virus, the herpes simplex virus, and the human herpes virus type 8 (HHV-8).

The compounds of the present invention may also useful for the treatment of several cardiovascular diseases such as atherosclerosis and restenosis. These diseases have been implicated connecting with inflammation of coronary vessel walls resulting from infection or reactivation of herpesviruses.

The compounds of the present invention may also be useful for the treatment of herpesvirus infections in animals, for example, illnesses caused by bovine herpesvirus 1–5 (BHV), ovine herpesvirus 1 and 2, Canine herpesvirus 1 equine herpesvirus 1–8 (EHV), feline herpesvirus 1 (FHV), and pseudorabies virus (PRV).

Pharmaceutical Salts

The compound of formula I may be used in its native form or as a salt. In cases where forming a stable nontoxic salt is desired, administration of the compound as a pharmaceutically acceptable salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, ketoglutarate, and glycerophosphate. Suitable inorganic salts may also be formed, including hydrochloride, hydrobromide, sulfate, nitrate, bicarbonate, and carbonate salts.

Pharmaceutically acceptable salts may be obtained using standard procedures well known in the art, for example by reacting a compound of the invention with a suitable acid affording a physiologically acceptable anion.

Routes of Administration

In therapeutic use for treating, or combating, viral infections in a mammal (i.e. human and animals) a compound of the present invention, its pharmaceutical compositions and other antiviral agents can be administered orally, parenterally, topically, rectally, transmucosally, or intestinally.

Parenteral administrations include indirect injections to generate a systemic effect or direct injections to the afflicted area. Examples of parenteral administrations are subcutaneous, intravenous, intramuscular, intradermal, intrathecal, intraocular, intranasal, intravetricular injections or infusions techniques.

Topical administrations include the treatment of infectious areas or organs readily accessibly by local application, such as, for example, eyes, ears including external and middle ear infections, vaginal, open wound, skins including the surface skin and the underneath dermal structures, or other lower intestinal tract. It also includes transdermal delivery to generate a systemic effect.

The rectal administration includes the form of suppositories.

The transmucosal administration includes nasal aerosol or inhalation applications.

The preferred routes of administration are oral and parenteral.

Composition/Formulation

Pharmaceutical compositions of the present invention may be manufactured by processes well known in the art, e.g., by means of conventional mixing, dissolving, granulation, dragee-making, levigating, emulsifying, encapsulating, entrapping, lyophilizing processes or spray drying.

Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, solutions, emulsions, gels, syrups, slurries, suspensions and the like, for oral ingestion by a patient. A carrier can be at least one substance which may also function as a diluent, flavoring agent, solubilizer, lubricant, suspending agent, binder, tablet disintegrating agent, and encapsulating agent. Examples of such carriers or excipients include, but are not limited to, magnesium carbonate, magnesium stearate, talc, sugar, lactose, sucrose, pectin, dextrin, mannitol, sorbitol, starches, gelatin, cellulosic materials, low melting wax, cocoa butter or powder, polymers such as polyethylene glycols and other pharmaceutical acceptable materials.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, liquid polyethylene glycols, cremophor, capmul, medium or long chain mono-, di- or triglycerides. Stabilizers may be added in these formulations, also.

Liquid form compositions include solutions, suspensions and emulsions. For example, there may be provided solutions of the compounds of this invention dissolved in water and water-propylene glycol and water-polyethylene glycol systems, optionally containing suitable conventional coloring agents, flavoring agents, stabilizers and thickening agents.

The compounds may also be formulated for parenteral administration, e.g., by injection, bolus injection or continuous infusion. Formulations for parenteral administration may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

For injection, the compounds of the invention may be formulated in aqueous solution, preferably in physiologically compatible buffers or physiological saline buffer. Suitable buffering agents include trisodium orthophosphate, sodium bicarbonate, sodium citrate, N-methylglucamine, L(+)-lysine and L(+)-arginine.

Parenteral administrations also include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water, before use. For suppository administration, the compounds may also be formulated by mixing the agent with a suitable non-irritating excipient which is solid at room temperature but liquid at rectal temperature and therefore will melt in the rectum to release the drug. Such materials include cocoa butter, beeswax and other glycerides.

For administration by inhalation, compounds of the present invention can be conveniently delivered through an aerosol spray in the form of solution, dry powder, or suspensions. The aerosol may use a pressurized pack or a nebulizer and a suitable propellant. In the case of a pressurized aerosol, the dosage unit may be controlled by providing a valve to deliver a metered amount. Capsules and cartridges of, for example, gelatin for use in an inhaler may be formulated containing a power base such as lactose or starch.

For topical applications, the pharmaceutical composition may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion such as suspensions, emulsion, or cream containing the active components suspended or dissolved in one or more pharmaceutically acceptable carriers. Suitable carriers include, but are not limited to, mineral oil, sorbitan monostearate, polysorbate 60, cetyl esters wax, ceteary alcohol, 2-octyldodecanol, benzyl alcohol and water.

For ophthalmic and otitis uses, the pharmaceutical compositions may be formulated as micronized suspensions in isotonic, pH adjusted sterile saline, or preferably, as solutions in isotonic, pH adjusted sterile saline, either with or without a preservative such as a benzylalkonium chloride. Alternatively, for ophthalmic uses, the pharmaceutical compositions may be formulated in an ointment such as petrolatum.

In addition to the formulations described previously, the compounds may also be formulated as depot preparations. Such long acting formulations may be in the form of implants. A compound of this invention may be formulated for this route of administration with suitable polymers, hydrophobic materials, or as a sparing soluble derivative such as, without limitation, a sparingly soluble salt.

Additionally, the compounds may be delivered using a sustained-release system. Various sustained-release materials have been established and are well known by those skilled in the art. Sustained-release capsules may, depending on their chemical nature, release the compounds for 24 hours or for up to several days.

Dosage

Pharmaceutical compositions suitable for use in the present invention include compositions wherein the active ingredients are contained in an amount sufficient to achieve the intended purpose, i.e., the treatment or prevention of infectious diseases. More specifically, a therapeutically effective amount means an amount of compound effective to prevent, alleviate or ameliorate symptoms of disease or prolong the survival of the subject being treated.

The quantity of active component, that is the compound of this invention, in the pharmaceutical composition and unit dosage form thereof may be varied or adjusted widely depending upon the manner of administration, the potency of the particular compound and the desired concentration. Determination of a therapeutically effective amount is well within the capability of those skilled in the art. Generally, the quantity of active component will range between 0.5% to 90% by weight of the composition.

Generally, an antiviral effective amount of dosage of active component will be in the range of about 0.1 to about 400 mg/kg of body weight/day, more preferably about 1.0 to about 50 mg/kg of body weight/day. It is to be understood that the dosages may vary depending upon the requirements of each subject and the severity of the viral infection being treated.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Also, it is to be understood that the initial dosage administered may be increased beyond the above upper level in order to rapidly achieve the desired plasma concentration. On the other hand, the initial dosage may be smaller than the optimum and the daily dosage may be progressively increased during the course of treatment depending on the particular situation. If desired, the daily dose may also be divided into multiple doses for administration, e.g., two to four times per day.

In cases of local administration or selective uptake, the effective local concentration of the drug may not be related to plasma concentration and other procedures know in the art may be used to determine the desired dosage amount.

Biological Data

While many of the compounds of the present invention have shown activity against the CMV polymerase, these compounds may be active against the cytomegalovirus by this or other mechanisms of action. Thus, the description below of these compounds' activity against the CMV polymerase is not meant to limit the present invention to a specific mechanism of action.

The compounds of the present invention have shown activity in one or more of the assays described below. All of these assays are indicative of a compound's activity and thus of its use as an anti-viral agent.

The HCMV polymerase assay is performed using a scintillation proximity assay (SPA) as described in several references, such as N. D. Cook, et al., Pharmaceutical Manufacturing International, pages 49–53 (1992); K. Takeuchi, Laboratory Practice, September issue (1992); U.S. Pat. No. 4,568,649 (1986); which are incorporated by reference herein. Reactions are performed in 96-well plates. The assay is conducted in 100 μl volume with 5.4 mM HEPES (pH 7.5), 11.7 mM KCl, 4.5 mM MgCl2, 0.36 mg/ml BSA, and 90 nM 3H-dTTP. Assays are run with and without CHAPS, (3-[(3-Cholamidopropyl)-dimethylammonio]-1-propane-sulfonate) at a final concentration of 2 mM. HCMV polymerase is diluted in enzyme dilution buffer containing 50% glycerol, 250 mM NaCl, 10 mM HEPES (pH 7.5), 100 μg/ml BSA, and 0.01% sodium azide. The HCMV polymerase, which is expressed in recombinant baculovirus-infected SF-9 cells and purified according to literature procedures, is added at 10% (or 10 μl) of the final reaction volume, i.e., 100 μl. Compounds are diluted in 50% DMSO and 10 μl are added to each well. Control wells contain an equivalent concentration of DMSO. Unless noted otherwise, reactions are initiated via the addition of 6 nM biotinylated poly(dA)-oligo(dT) template/primer to reaction mixtures containing the enzyme, substrate, and compounds of interest. Plates are incubated in a 25 C. or 37 C. H2O bath and terminated via the addition of 40 μl/reaction of 0.5 M EDTA (pH 8) per well. Reactions are terminated within the time-frame during which substrate incorporation is linear and varied depending upon the enzyme and conditions used, i.e., 30 min. for HCMV polymerase. Ten μl of streptavidin-SPA beads (20 mg/ml in PBS/10%) are added following termination of the reaction. Plates are incubated 10 min. at 37 C., then equilibrated to room temperature, and counted on a Packard Topcount. Linear regressions are performed and IC50's are calculated using computer software.

A modified version of the above HCMV polymerase assay is performed as described above, but with the following changes: Compounds are diluted in 100% DMSO until final dilution into assay buffer. In the previous assay, compounds are diluted in 50% DMSO. 4.5 mM dithiotherotol (DTT) is added to the polymerase buffer. Also, a different lot of CMV polymerase is used, which appears to be more active resulting in a more rapid polymerase reaction.

Results of the testing of compounds of the present invention in this assay are shown in Table b 1below.

All results are listed as Polymerase IC50 ($\mu$M) values. In Table 1, the term "n.d." refers to activity data not determined.

TABLE 1

| | Polymerase IC$_{50}$ ($\mu$M) | | |
|---|---|---|---|
| Example number | CMV | HSV | VZV |
| 1 | 0.32 | 0.25 | 0.18 |
| 2 | 0.32 | n.d. | n.d. |
| 3 | 0.87 | n.d. | n.d. |
| 4 | 0.83 | 0.83 | 0.36 |
| 5 | 1.6 | n.d. | n.d. |
| 6 | 0.8 | 0.82 | 0.36 |
| 7 | 0.76 | 0.45 | 0.18 |
| 8 | 0.87 | 1 | 0.48 |
| 9 | 0.55 | n.d. | n.d. |
| 10 | 0.48 | 0.41 | 0.16 |
| 11 | 0.36 | 0.28 | 0.18 |
| 12 | 0.77 | n.d. | n.d. |
| 13 | 0.50 | 0.49 | 0.25 |
| 14 | 0.52 | n.d. | n.d. |
| 15 | 0.32 | 0.26 | 0.14 |
| 16 | 0.47 | 0.28 | 0.15 |
| 17 | 0.42 | 0.21 | 0.11 |
| 18 | 0.61 | n.d. | n.d. |
| 19 | 1.01 | n.d. | n.d. |
| 20 | 1.02 | n.d. | n.d. |
| 21 | 0.80 | n.d. | n.d. |
| 22 | 0.82 | n.d. | n.d. |
| 23 | 0.33 | 0.22 | 0.10 |
| 24 | 0.56 | n.d. | n.d. |
| 25 | 0.74 | n.d. | n.d. |
| 26 | 1.29 | n.d. | n.d. |
| 27 | 0.94 | n.d. | n.d. |
| 28 | 0.82 | n.d. | n.d. |
| 29 | 0.73 | n.d. | n.d. |
| 30 | 0.71 | n.d. | n.d. |
| 31 | 0.49 | 0.55 | 0.33 |

The compounds and their preparation of the present invention will be better understood in connection with the following examples, which are intended as an illustration of and not a limitation upon the scope of the invention.

EXAMPLES

Preparation 1

(4-nitrobenzyl)(triphenyl)phosphonium Bromide

To a solution of triphenylphosphine (25.92 g) in 300 mL CH2Cl2 is added 4-nitrobenzylbromide (31.47 g). The solution is allowed to stir overnight. The mixture is concentrated. The resulting solid is triturated with Et2O, filtered and dried to yield 54.58 g (95%) of the desired product as a white solid.

Physical characteristics are as follows: 1H NMR (CDCl3) δ 7.81, 7.75, 7.61, 7.47, 5.99.

Preparation 2

4-(4-nitrobenzylidene)tetrahydro-2H-pyran

To a 500 mL 3-necked flask is added NaH (2.0 g of a 60% suspension in mineral oil) and 35 mL of DMSO. The resulting solution is heated at 80° C. for 1 h then cooled in an ice-water bath. To this is then added a solution of the phosphonium bromide (23.92 g) in 200 mL warm DMSO. The mixture is stirred at room temperature for 1 h. Tetrahydro-4H-pyran-4-one (4.62 mL) is then added. The mixture is allowed to stir overnight at room temperature and then at 80° C. for 2 days. The mixture is poured over ice and extracted with Et2O. The combined organic extracts are dried and condensed. Chromatography (Biotage flash 40S, gradient from hexanes to 80% CH2Cl2/hexanes) yields 4.83 g (44%) of the desired product as a bright yellow solid.

Physical characteristics are as follows: 1H NMR (CDCl3) δ 8.19, 7.35, 6.38, 3.82, 3.70, 2.55, 2.46.

Preparation 3

2-iodo-4-(tetrahydro-2H-pyran-4-ylmethyl)aniline

A mixture of 4-(4-nitrobenzylidene)tetrahydro-2H-pyran (2.0 g) and PtO2 (0.2 g) is hydrogenated at 40 p.s.i. H2 for 3.5 h. The mixture is filtered through celite and the filtrate condensed. The crude residue is dissolved in a mixture of 40 mL CHCl3 and 4 mL MeOH. To this is added sodium acetate (2.24 g), followed by the dropwise addition of a solution of ICl (0.69 mL) in MeOH (10 mL). The reaction is stirred at room temperature for 1 h then quenched by pouring into an iced saturated solution of aqueous sodium bisulfite (200 mL). The mixture is stirred for 30 minutes then concentrated until all of the organics are gone. The aqueous solution is extracted with CH2Cl2 (3×). The combined organic layers are washed with brine, dried and condensed. The crude product is chromatographed (Biotage flash 40M, eluent CH2Cl2) to yield 1.0 g (34%) of the desired product as a yellow oil.

Physical characteristics are as follows: 1H NMR (CDCl3) δ 7.47, 6.95, 6.76, 3.95, 3.34, 2.41, 1.68, 1.56, 1.31; OAMS supporting ions at: ESI+318.1.

Preparation 4

Ethyl 4-hydroxy-8-iodo-6-(tetrahydro-2H-pyran-4-ylmethyl)-3-quinolinecarboxylate A mixture of 2-iodo-4-(tetrahydro-2H-pyran-4-ylmethyl) aniline (1.0 g) and diethyl ethoxymethylenemalonate (0.70 mL) is heated at 130° C. for 1 h. The mixture is cooled to room temperature. Diphenyl ether (20 mL) is added and the reaction is heated to 250° C. for 1 h. The mixture is cooled and the resulting solid is collected and washed with hexanes. The crude product is chromatographed (Biotage flash 40M, eluent 2% MeOH/CH2Cl2) to yield 0.80 g (58%) of the desired product as an off-white solid.

Physical characteristics are as follows: m.p. 218–222° C. (dec); 1H NMR (DMSO-d6) δ 11.18, 8.45, 8.09, 7.95, 4.22, 3.80, 3.22, 2.61, 1.76, 1.45, 1.27, 1.20; IR (drift) 3073, 2928, 2918, 1709, 1619, 1600, 1560, 1517, 1327, 1292, 1216, 1170, 1154, 1135, 1090 cm−1. OAMS supporting ions at: ESI+442.0 ESI−441.0; HRMS (FAB) calcd for C18H20INO4+H1 442.0517, found 442.0526; Anal. calcd for C18H20INO4: C, 48.99; H, 4.57; N, 3.17, found: C, 49.09; H, 4.58; N, 3.24.

Preparation 5

N-(4-chlorobenzyl)-4-hydroxy-8-iodo-6-(tetrahydro-2H-pyran-4-ylmethyl)-3-quinolinecarboxamide A suspension of ethyl 4-hydroxy-8-iodo-6-(tetrahydro-2H-pyran-4-ylmethyl)-3-quinolinecarboxylate (0.8 g) and 4-chlorobenzylamine (1.54 mL) is heated to 180° C. for 1 h. The reaction is cooled to room temperature. The resulting solid is collected and washed with Et2O. The crude solid is adsorbed onto silica and chromatographed (Biotage flash 40S, eluent 1% MeOH/CH2Cl2 then 2% MeOH/CH2Cl2). Fractions homogeneous by TLC are combined and concentrated. The resulting solid is triturated with EtOAc/hexanes to yield 0.73 g (75%) of the desired product as a white solid.

Physical characteristics are as follows: m.p. 257–259° C.; 1H NMR (DMSO-d6) δ 10.39, 8.70, 8.15, 8.04, 7.38, 4.54, 3.80, 3.22, 2.63, 1.79, 1.48, 1.24; IR (drift) 2925, 1654, 1596, 1554, 1513, 1493, 1099, 1090, 850, 828, 811, 799, 781, 766, 724 cm−1; OAMS supporting ions at: ESI+536.7 ESI−534.7; Anal. calcd for C23H22ClIN2O3: C, 51.46; H, 4.13; N, 5.22, found: C, 51.31; H, 4.13; N, 5.20.

Preparation 6

N-(4-chlorobenzyl)-8-iodo-1-methyl-4-oxo-6-(tetrahydro-2H-pyran-4-ylmethyl)-1,4-dihydro-3-quinolinecarboxamide To a mixture of N-(4-chlorobenzyl)-4-hydroxy-8-iodo-6-(tetrahydro-2H-pyran-4-ylmethyl)-3-quinolinecarboxamide (0.075 g) and K2CO3 (0.077 g) in 5 mL DMF is added methyl iodide (2.4 g) and the mixture is stirred at room temperature for 5 days. The mixture is then poured into water and the resulting solid collected. The crude product is chromatographed (Biotage flash 40S, eluent CH2Cl2 then 1% MeOH/CH2Cl2). Fractions homogeneous by TLC are combined and concentrated. The resulting solid is recrystallized from CH2Cl2/hexanes to yield 0.037 g (48%) of the desired product as a white solid.

Physical characteristics are as follows: m.p. 175–177° C.; 1H NMR (DMSO-d6) δ 10.21, 8.75, 8.37, 8.16, 7.37, 4.55, 4.38, 3.80, 3.22, 2.62, 1.75, 1.45, 1.20; IR (diffuse reflectance) 2926, 1658, 1598, 1575, 1538, 1489, 1459, 1360, 1243, 1234, 1134, 1103, 1091, 1015, 808 cm−1; MS (EI) m/z 550 (M+), 550, 410, 384, 383, 257, 142, 142, 140, 115, 55; Anal. calcd for C24H24ClIN2O3: C, 52.33; H, 4.39; N, 5.09; found: C, 52.09; H, 4.36; N, 5.09.

Example 1

N-(4-chlorobenzyl)-8-(3-hydroxy-1-propynyl)-1-methyl-4-oxo-6-(tetrahydro-2H-pyran-4-ylmethyl)-1,4-dihydro-3-quinolinecarboxamide

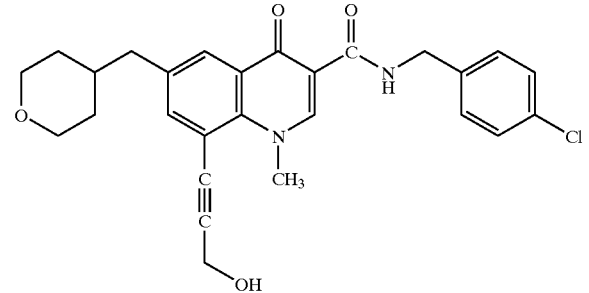

To a solution of N-(4-chlorobenzyl)-8-iodo-1-methyl-4-oxo-6-(tetrahydro-2H-pyran-4-ylmethyl)-1,4-dihydro-3-quinolinecarboxamide (0.200 g), PdCl2(PPh3)2 (0.012 g) and CuI (0.029 g) in 10 mL Et2NH and 5 mL CH2Cl2 is added propargyl alcohol (0.021 g). The mixture is allowed to stir overnight at room temperature. The solvents are evaporated and the residue is partitioned between CH2Cl2 and water. The aqueous layer is extracted with CH2Cl2 (3×). The combined organic layers are washed with brine, dried and condensed. The crude product is chromatographed (Biotage flash 40S, eluent 1% MeOH/CH2Cl2 then 2% MeOH/CH2Cl2). Fractions homogeneous by TLC are combined and concentrated. The resulting solid is recrystallized from CH2Cl2/Et2O to yield 0.114 g (66%) of the desired product as a white solid.

Physical characteristics are as follows: m.p. 166–168° C.; 1H NMR (DMSO-d6) δ 10.29, 8.74, 8.15, 7.77, 7.38, 5.42, 4.56, 4.42, 4.39, 3.80, 3.22, 2.65, 1.77, 1.45, 1.24; IR (diffuse reflectance) 2916, 2850, 1657, 1603, 1556, 1489, 1408, 1359, 1244, 1131, 1109, 1088, 1014, 849, 810 cm−1; MS (EI) m/z 478 (M+), 338, 312, 311, 226, 140, 125, 89, 77, 56, 55; HRMS (FAB) calcd for C27H27ClN2O4+H1 479.1737, found 479.1735; Anal. calcd for C27H27ClN2O4: C, 67.71; H, 5.68; N, 5.85; found: C, 67.31; H, 5.73; N, 5.74.

Example 2

N-(4-chlorobenzyl)-8-(4-hydroxy-1-butynyl)-1-methyl-4-oxo-6-(tetrahydro-2H-pyran-4-ylmethyl)-1,4-dihydro-3-quinolinecarboxamide

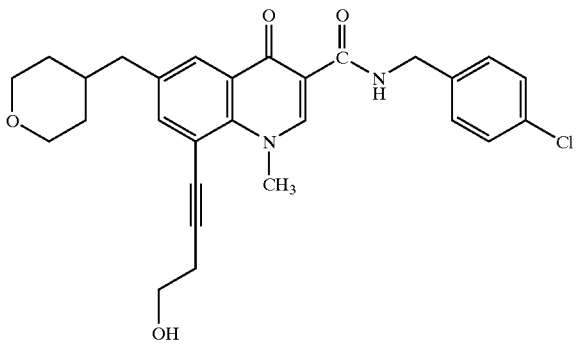

A solution of N-(4-chlorobenzyl)-8-iodo-1-methyl-4-oxo-6-(tetrahydro-2H-pyran-4-ylmethyl)-1,4-dihydro-3-quinolinecarboxamide (0.074 g), copper iodide (0.013 g), Pd(PPh3)2Cl2 (0.007 g) and 3-butyn-1-ol (0.02 mL) in 7 mL diethylamine is stirred at room temperature for 3 days. The reaction is partitioned between CH2Cl2 and H2O. The aqueous is extracted 3×with CH2Cl2. The organics are combined, dried over Na2SO4, filtered and concentrated. The residue is dissolved in CH2Cl2 and adsorbed onto silica. Purification by Biotage Flash 40S chromatography (eluent CH2Cl2 (1L), 0.5% MeOH/CH2Cl2 (1L), 1% MeOH/CH2Cl2 (1L), 1.5% MeOH/CH2Cl2 (1L), 2% MeOH/CH2Cl2 (1L), 3% MeOH/CH2Cl2 (1L), 5% MeOH/CH2Cl2 (1L), 7% MeOH/CH2Cl2 (1L)) affords the product as a tan residue. The residue is dissolved in a minimal amount of CH2Cl2 and hexanes are added to affect recrystallization. The solution is placed in the freezer for 18 h after which the product is collected and dried (0.037 g, 57%).

Physical characteristics are as follows: m.p. 186–188° C.; 1H NMR (300 MHz, DMSO-d6) δ 10.31, 8.73, 8.13, 7.76, 7.40, 7.36, 4.96, 4.55, 4.43, 3.80, 3.64, 3.22, 2.64, 1.77, 1.43, 1.22; IR (drift) 2917, 1656, 1603, 1556, 1492, 1446, 1361, 1231, 1127, 1086, 1056, 845, 808, 744, 703 cm−1; MS (FAB) m/z 493, 495, 494, 493, 492, 353, 352, 350, 219, 127, 125.

Example 3

N-(4-chlorobenzyl)-8-[3-(dimethylamino)-1-propynyl]-1-methyl-4-oxo-6-(tetrahydro-2H-pyran-4-ylmethyl)-1,4-dihydro-3-quinolinecarboxamide

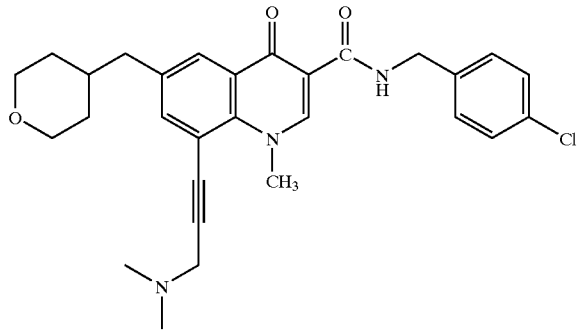

A solution of N-(4-chlorobenzyl)-8-iodo-1-methyl-4-oxo-6-(tetrahydro-2H-pyran-4-ylmethyl)-1,4-dihydro-3-quinolinecarboxamide (0.070 g), copper iodide (0.013 g), Pd(PPh3)2Cl2 (0.007 g) and N,N-dimethylpropargylamine (0.020 mL) in 7 mL diethylamine is stirred at room temperature for 3 days. The reaction is partitioned between CH2Cl2 and H2O. The aqueous layer is extracted 3×with CH2Cl2. The organics are combined, dried over Na2SO4, filtered and concentrated. The residue is dissolved in CH2Cl2 and adsorbed onto silica. Purification by Biotage Flash 40S (eluent CH2Cl2 (1L), 1% MeOH/CH2Cl2 (1L), 2% MeOH/CH2Cl2 (1L), 3% MeOH/CH2Cl2 (1L), 4% MeOH/CH2Cl2 (1L), 5% MeOH/CH2Cl2 (1L)) affords the product as a tan residue. Recrystallization with CH2Cl2/hexanes affords the desired product (0.046 g, 70%).

Physical characteristics are as follows: m.p. 157–159° C.; 1H NMR (300 MHz, DMSO-d6) δ 8.74, 8.16, 7.81, 7.40, 7.36, 4.56, 4.44, 3.80, 3.57, 3.22, 2.66, 2.31, 1.77, 1.45, 1.23; IR (drift) 2916, 2852, 1656, 1604, 1552, 1490, 1466, 1448, 1360, 1243, 1133, 1128, 1091, 1014, 808 cm−1; MS (FAB) m/z 506, 509, 508, 507, 506, 505, 504, 365, 338, 125, 58; HRMS (FAB) calcd for C29H32ClN3O3+H 1 506.2210, found 506.2202.

Preparation 7

Ethyl 4-amino-3-iodobenzoate

To a solution of ethyl 4-aminobenzoate (13.0 g) in DMF (33 mL) is added a solution of N-iodosuccinimide (18.6 g) in DMF (39 mL). The reaction is stirred at room temperature overnight. The mixture is poured into 800 mL water. The resulting solid is collected and dried to yield 20.7 g (90%) of the titled compound.

Physical characteristics are as follows: m.p. 71–74° C.; 1H NMR (300 MHz, DMSO-d6) δ 8.10, 7.65, 6.74, 4.21, 1.27; IR (drift) 3455, 3364, 1688, 1615, 1592, 1364, 1324, 1292, 1286, 1249, 1152, 1127, 818, 762, 671 cm−1; OAMS supporting ions at: ESI+291.9 ESI−289.9; Anal. calcd for C9H10INO2: C, 37.14; H, 3.46; N, 4.81, found: C, 37.02; H, 3.44; N, 4.81.

Preparation 8

(4-amino-3-iodophenyl)methanol

To a solution of ethyl 4-amino-3-iodobenzoate (8.0 g) in CH2Cl2 (56 mL) cooled to 0° C. is added diisobutylaluminum hydride in CH2Cl2 (110 mL of a 1M solution). The reaction is stirred at 0° C. for 2 h then quenched by the addition of MeOH (50 mL). To this is added 1N HCl (100 mL). The mixture is concentrated to remove the organics. The aqueous solution is extracted with CH2Cl2 (3×). The combined organic layers are dried over Na2SO4, filtered and condensed. The resulting residue is adsorbed onto silica and chromatographed (Biotage flash 40M, eluent CH2Cl2 (2L), 1% MeOH/CH2Cl2 (2L), 2% MeOH/CH2Cl2). Fractions homogeneous by TLC are combined and condensed to afford (4-amino-3-iodophenyl)methanol.

Physical characteristics are as follows: 1H NMR (300 MHz, DMSO-d6) δ 7.49, 7.01, 6.70, 6.00, 4.95, 4.28.

Preparation 9 diethyl 2-{[4-(hydroxymethyl)-2-iodoanilino]methylene}malonate

A solution of (4-amino-3-iodophenyl)methanol (5.97 g) and diethyl ethoxymethylenemalonate (5.34 mL) is heated at 100° C. for 30 min. The reaction is cooled to room temperature. The resulting solid is dissolved in a mixture of CH2Cl2 and MeOH, adsorbed onto silica and chromatographed (Biotage flash 40M, eluent CH2Cl2 (1L), 0.5% MeOH/CH2Cl2 (5L)). Product containing fractions are combined and condensed to afford diethyl 2-{[4-(hydroxymethyl)-2-iodoanilino]methylene}malonate as a white solid.

Physical characteristics are as follows: m.p. 152–154° C.; 1H NMR (300 MHz, DMSO-d6) δ 11.0, 8.43, 7.83, 7.47, 7.38, 5.29, 4.45, 4.23, 4.14, 1.27, 1.25; IR (drift) 1680, 1644, 1593, 1423, 1384, 1373, 1349, 1296, 1285, 1267, 1242, 1202, 1036, 1004, 798 cm–1; OAMS supporting ions at: ESI+419.7 ESI–417.8; Anal. calcd for C15H18INO5: C, 42.98; H, 4.33; N, 3.34, found: C, 42.73; H, 4.21; N, 3.33.

Preparation 10 diethyl 2-({4-[(acetyloxy)methyl]-2-iodoanilino}methylene)malonate

A solution of diethyl 2-{[4-(hydroxymethyl)-2-iodoanilino]methylene}malonate (0.20 g) and acetic anhydride (0.054 mL) in acetic acid (0.24 mL) is heated at 80° C. overnight. The reaction is cooled to room temperature and poured into 50 mL of water. The resulting solid is filtered and dried to yield 0.19 g (87%) of diethyl 2-({4-[(acetyloxy)methyl]-2-iodoanilino}methylene)malonate as a white solid.

Physical characteristics are as follows: m.p. 128–131° C.; 1H NMR (300 MHz, DMSO-d6) δ 10.99, 8.44, 7.91, 7.51, 7.44, 5.01, 4.24, 4.14, 2.06, 1.27, 1.25; IR (drift) 1737, 1686, 1648, 1600, 1428, 1362, 1349, 1299, 1267, 1248, 1209, 1039, 1023, 809, 797 cm–1; OAMS supporting ions at: EST+461.7 ESI–459.7; Anal. Calcd for C17H20INO6: C, 44.27; H, 4.37; N, 3.04, found: C, 44.39; H, 4.37; N, 3.09.

Preparation 11 ethyl 6-[(acetyloxy)methyl]-4-hydroxy-8-iodo-3-quinolinecarboxylate

A solution of diethyl 2-({4-[(acetyloxy)methyl]-2-iodoanilino}methylene) malonate (1.75 g) in Ph2O (20 mL) is heated at 250° C. for 40 min. The reaction is cooled to room temperature and diluted with hexanes. The resulting solid is collected and dried. The crude solid is adsorbed onto silica and chromatographed (Biotage flash 40S, eluent CH2Cl2 (1L), 1% MeOH/CH2Cl2 (1L), 2% MeOH/ CH2Cl2 (1L). Product containing fractions are combined and concentrated to yield 0.98 g (62%) of ethyl 6-[(acetyloxy)methyl]-4-hydroxy-8-iodo-3-quinolinecarboxylate.

Physical characteristics are as follows: m.p. 119–123° C.; 1H NMR (300 MHz, DMSO-d6) δ 11.29, 8.48, 8.23, 8.16, 5.15, 4.23, 2.09, 1.28; IR (drift) 2993, 2956, 1738, 1711, 1602, 1550, 1524, 1331, 1293, 1284, 1242, 1218, 1172, 1093, 1035 cm–1; OAMS supporting ions at: ESI+415.8 ESI–413.9; HRMS (FAB) calcd for C15H14INO5+H1 415.9997, found 416.0000; Anal. Calcd for C15H14INO5: C, 43.39; H, 3.40; N, 3.37, found: C, 43.55; H, 3.39; N, 3.73.

Preparation 12

N-(4-chlorobenzyl)-4-hydroxy-6-(hydroxymethyl)-8-iodo-3-quinolinecarboxamide

A suspension of ethyl 6-[(acetyloxy)methyl]-4-hydroxy-8-iodo-3-quinolinecarboxylate (0.90 g) and 4-chlorobenzylamine (2.6 mL) is heated at 180° C. for 1 h. The reaction is cooled to room temperature and diluted with Et2O. The resulting solid is filtered and triturated with acetone to yield 0.74 g (73%) of N-(4-chlorobenzyl)-4-hydroxy-6-(hydroxymethyl)-8-iodo-3-quinolinecarboxamide.

Physical characteristics are as follows: m.p. 283–286° C.; 1H NMR (300 MHz, DMSO-d6) δ 11.61, 10.29, 8.71, 8.23, 7.38, 5.46, 4.60, 4.55; IR (drift) 3369, 3235, 1654, 1598, 1556, 1517, 1491, 1351, 1281, 1213, 1181, 1069, 811, 799, 723 cm–1; OAMS supporting ions at: ESI+468.6 ESI–466.6; Anal. calcd for C18H14ClIN2O3: C, 46.13; H, 3.01; N, 5.98, found: C, 46.12; H, 2.99; N, 5.99.

Preparation 13

N-(4-chlorobenzyl)-6-(hydroxymethyl)-8-iodo-1-methyl-4-oxo-1,4-dihydro-3-quinolinecarboxamide A solution of N-(4-chlorobenzyl)-4-hydroxy-6-(hydroxymethyl)-8-iodo-3-quinolinecarboxamide(6.5 g) in anhydrous DMF (116.7 mL) is heated to 65° C. to solubilize the starting material. The solution is allowed to cool to room temperature. To this solution is added K2CO3 (7.68 g) and CH3I (8.65 mL). The reaction is stirred at room temperature overnight. The reaction is poured into H2O (1L) to precipitate the product. The solid is filtered, adsorbed onto silica, and chromatographed in 2 batches (eluent 100% CH2Cl2 (3L), 0.5% MeOH in CH2Cl2 (1L), and 1% MeOH in CH2Cl2 (9L)). Product-containing fractions are combined and condensed to afford 3.6 g (54%) of the desired product as a white solid.

Physical characteristics are as follows: m.p. 242–244° C.; 1H NMR (300 MHz, DMSO-d6) δ 10.21, 8.76, 8.44, 8.33, 7.40, 5.48, 4.59, 4.56, 4.39; IR (drift) 1658, 1599, 1579, 1551, 1492, 1457, 1359, 1120, 1114, 1091, 1017, 806, 740, 693, 672 cm–1; MS (ESI) for m/z 482.9 (M+H)+; Anal calcd for C19H16ClIN2O3: C, 47.28; H, 3.34; N, 5.80. Found: C, 47.42; H, 3.36; N, 5.77.

Preparation 14

N-(4-chlorobenzyl)-6-(chloromethyl)-8-iodo-1-methyl-4-oxo-1,4-dihydro-3-quinolinecarboxamide A solution of N-(4-chlorobenzyl)-6-(hydroxymethyl)-8-iodo-1-methyl-4-oxo-1,4-dihydro-3-quinolinecarboxamide (4.89 g), DMAP (209 mg) and collidine (1.59 mL) in 173 mL anhydrous DMF is heated to 65° C. to solubilize the starting material. To this solution is added methanesulfonyl chloride (2.77 mL) at room temperature. The reaction is heated at 65° C. for 2 h, then allowed to cool to room temperature. The reaction is poured into H2O (300 mL) to precipitate the product. The solid is filtered and recrystallized from CH2Cl2/hexanes to afford 4.74 g (93%) of the desired product as a white solid.

Physical characteristics are as follows: m.p. 237–239° C.; 1H NMR (300 MHz, DMSO-d6) δ 10.14, 8.78, 8.57, 8.43, 7.38, 4.91, 4.56, 4.40; IR (drift) 3051, 1661, 1599, 1577, 1552, 1491, 1401, 1357, 1261, 1115, 1106, 1092, 807, 799, 710 cm−1; MS (ESI) for m/z 500.7 (M+H)+; Anal calcd for C19H15Cl2IN2O2: C, 45.54; H, 3.02; N, 5.59. Found: C, 45.50; H, 3.05; N, 5.58.

Preparation 15

N-(4-chlorobenzyl)-8-iodo-1-methyl-6-(4-morpholinylmethyl)-4-oxo-1,4-dihydro-3-quinolinecarboxamide A solution of N-(4-chlorobenzyl)-6-(chloromethyl)-8-iodo-1-methyl-4-oxo-1,4-dihydro-3-quinolinecarboxamide (3.95 g), N,N-diisopropylethylamine (1.79 mL), and morpholine (0.96 mL) in anhydrous DMF (149 mL) is heated at 65° C. for 1–2 h. The reaction is allowed to cool to room temperature, then poured into H2O (300 mL) to precipitate the product. The solid is filtered, adsorbed onto silica, and chromatographed (eluent 100% CH2Cl2 (0.5% CH2Cl2 (1L), 1% MeOH in CH2Cl2 (1L), 1.5% MeOH in CH2Cl2 (1 L), 2% MeOH in CH2Cl2 (1L), 2.5% MeOH in CH2Cl2 (2L)). Product-containing fractions are combined and condensed to afford 3.17 g (73%) of the desired product as a white solid.

Physical characteristics are as follows: m.p. 156–158° C.; 1H NMR (300 MHz, DMSO-d6) δ 10.19, 8.77, 8.45, 8.30, 7.38, 4.55, 4.39, 3.58, 2.37; IR (drift) 1662, 1598, 1575, 1544, 1489, 1458, 1398,1360, 1347, 1333, 1243, 1114, 1015, 1008, 810 cm−1; MS (FAB) m/z 552, 554, 553, 552, 551, 550, 426, 425, 411, 125, 100; Anal calcd for C23H23ClIN3O3: C, 50.06; H, 4.20; N, 7.61. Found: C, 49.99; H, 4.15; N, 7.58.

Example 4

N-(4-chlorobenzyl)-8-(3-hydroxy-1-propynyl)-1-methyl-6-(4-morpholinylmethyl)-4-oxo-1,4-dihydro-3-quinolinecarboxamide

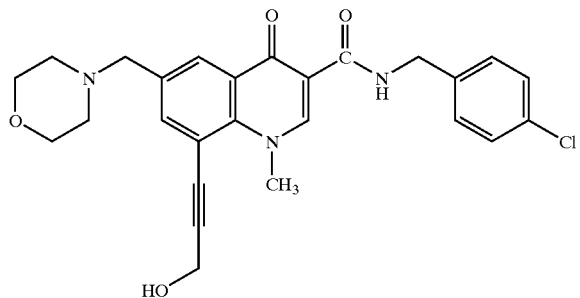

To a solution of N-(4-chlorobenzyl)-8-iodo-1-methyl-6-(4-morpholinylmethyl)-4-oxo-1,4-dihydro-3-quinolinecarboxamide (264 mg), PdCl2(PPh3)2 (17.3 mg), and CuI (4.7 mg) in 9.6 mL Et2NH is added propargyl alcohol (0.029 mL, 0.492 mmol). Distilled CH2Cl2 (14 mL) is added to help solublize the reactants. The reaction is stirred at room temperature overnight, then condensed to remove the solvents. The crude product is adsorbed onto silica and chromatographed (eluent 1% MeOH in CH2Cl2 (1L), 2% MeOH in CH2Cl2 (1L), and 3% MeOH in CH2Cl2 (2L)). Product-containing fractions are combined and condensed to afford 148.2 mg (63%) of the desired product as a tan solid.

Physical characteristics are as follows: m.p. 180–183° C.; 1H NMR (300 MHz, DMSO-d6) δ 10.27, 8.76, 8.28, 7.85, 7.38, 5.43, 4.56; 4.43, 4.39, 3.58; 2.37; IR (drift) 3415, 3364, 1662, 1602, 1578, 1551, 1492, 1432, 1361, 1352, 1330, 1114, 1017, 810, 799 cm−1; HRMS (FAB) calcd for C26H26ClN3O4+H1 480.1690, found 480.1697.

Example 5

N-(4-chlorobenzyl)-8-[3-(dimethylamino)-1-propynyl]-1-methyl-6-(4-morpholinylmethyl)-4-oxo-1,4-dihydro-3-quinolinecarboxamide

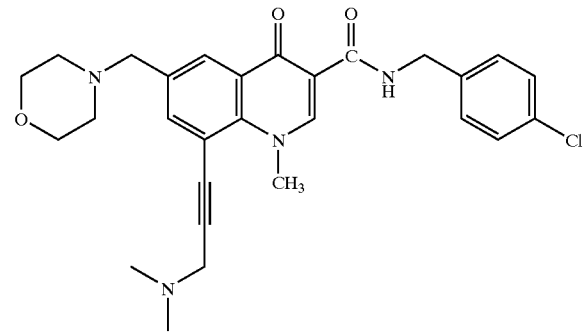

To a solution of N-(4-chlorobenzyl)-8-iodo-1-methyl-6-(4-morpholinylmethyl)-4-oxo-1,4-dihydro-3-quinolinecarboxamide (300 mg), PdCl2 (PPh3)2 (19.1 mg), and CuI (5.2 mg) in Et2NH (6.2 mL) is added 1-dimethylamino-2-propyne (0.065 mL). Anhydrous DMF (10 mL) is added to help solubilize the reactants (also requires sonication). The reaction is stirred at room temperature overnight, then condensed. The resulting residue is placed under high vac to remove residual DMF. The crude product is dissolved in CH2Cl2 and partitioned between CH2Cl2 and H2O. The aqueous layer is extracted with CH2Cl2 (2×). The combined organic layers are dried over Na2SO4, filtered, and condensed. The crude product is adsorbed onto silica and chromatographed (eluent 1% MeOH in CH2Cl2 (1L), 2% MeOH in CH2Cl2 (1L), 3% MeOH in CH2Cl2 (1L), 5% MeOH in CH2Cl2 (1L), and 6% MeOH in CH2Cl2 (1L)). Product-containing fractions are combined, concentrated, and recrystallized from hot acetonitrile to afford 153.5 mg (55%) of the desired product as a white solid.

Physical characteristics are as follows: m.p. 154–157° C.; 1H NMR (300 MHz, DMSO-d6) δ 10.27, 8.75, 8.29, 7.88, 7.38, 4.56, 4.44, 3.57, 2.37, 2.28; IR (drift) 2938, 2817, 2768, 1653, 1600, 1581, 1555, 1531, 1490, 1464, 1361, 1344, 1113, 886, 809 cm−1; Anal. calcd for C28H31ClN4O3: C, 66.33; H, 6.16; N, 11.05. Found: C, 66.07; H, 6.17; N, 11.04.

Example 6

N-(4-chlorobenzyl)-8-(4-hydroxy-1-butynyl)-1-methyl-6-(4-morpholinylmethyl)-4-oxo-1,4-dihydro-3-quinolinecarboxamide

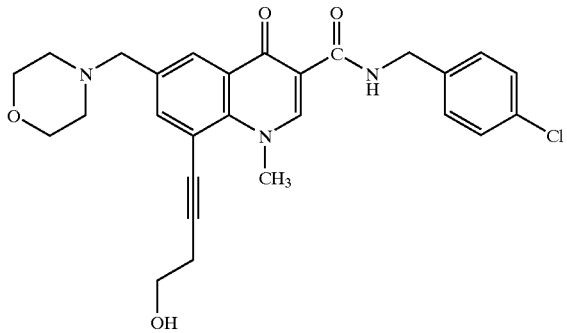

To a solution of N-(4-chlorobenzyl)-8-iodo-1-methyl-6-(4-morpholinylmethyl)-4-oxo-1,4-dihydro-3-quinolinecarboxamide (300 mg), PdCl2(PPh3)2 (19.1 mg), and CuI (5.2 mg) in Et2NH (6.2 mL) is added 1-dimethylamino-2-propyne (0.065 mL). Anhydrous DMF (10 mL) is added to help solubilize the reactants (also requires sonication). The reaction is stirred at room temperature overnight, then condensed. The resulting residue is placed under high vac to remove residual DMF. The crude product is dissolved in CH2Cl2 and partitioned between CH2Cl2 and H2O. The aqueous layer is extracted with CH2Cl2 (2×). The combined organic layers are dried over Na2SO4, filtered, and condensed. The crude product is adsorbed onto silica and chromatographed (eluent 100% CH2Cl2 (1L), 0.5% MeOH in CH2Cl2 (1L), 1% MeOH in CH2Cl2 (1L), 1.5% MeOH in CH2Cl2 (1L), 2% MeOH in CH2Cl2 (1L), and 2.5% MeOH in CH2Cl2 (3L)). Product-containing fractions are combined, concentrated, and recrystallized from hot acetonitrile to afford 125.6 mg (47%) of the desired product as a white solid.

Physical characteristics are as follows: m.p. 168–170° C.; 1H NMR (300 MHz, DMSO-d6) δ 10.29, 8.74, 8.25, 7.83; 7.38, 4.97, 4.55, 4.44, 3.64, 3.57, 2.65, 2.36; IR (drift) 1657, 1603, 1557, 1492, 1459, 1397, 1361, 1351, 1126, 1108, 1055, 1039, 859, 809, 794 cm−1; HRMS (FAB) calcd for C27H28ClN3O4+H1 494.1846, found 494.1838.

Example 7

N-(4-chlorobenzyl)-8-[(3S)-3-hydroxy-1-butynyl]-1-methyl-6-(4-morpholinylmethyl)-4-oxo-1,4-dihydro-3-quinolinecarboxamide

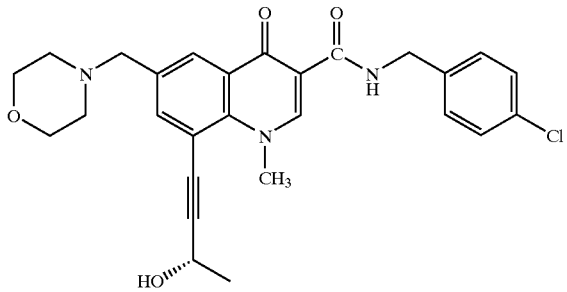

To a solution of N-(4-chlorobenzyl)-8-iodo-1-methyl-6-(4-morpholinylmethyl)-4-oxo-1,4-dihydro-3-quinolinecarboxamide (300 mg), PdCl2(PPh3)2 (19.1 mg), and CuI (5.2 mg) in Et2NH (6.2 mL) is added (R)-(+)-3-butyn-2-ol (0.047 mL, 0.599 mmol). Anhydrous DMF (10 mL) is added to help solubilize the reactants (also requires sonication). The reaction is stirred at room temperature overnight, then condensed. The resulting residue is placed under high vac to remove residual DMF. The crude product is dissolved in CH2Cl2 and partitioned between CH2Cl2 and H2O. The aqueous layer is extracted with CH2Cl2 (2×). The combined organic layers are dried over Na2SO4, filtered, and condensed. The crude product is adsorbed onto silica and chromatographed (eluent 100% CH2Cl2 (1L), 0.5% MeOH in CH2Cl2 (1L), 1% MeOH in CH2Cl2 (1L), 1.5% MeOH in CH2Cl2 (1L), and 2% MeOH in CH2Cl2 (4L)). Product-containing fractions are combined, concentrated, and recrystallized from hot acetonitrile to afford 90.7 mg (34%) of the desired product as a white solid.

Physical characteristics are as follows: m.p. 158–161° C.; 1H NMR (300 MHz, DMSO-d6) δ 10.28, 8.75, 8.27, 7.82, 7.38, 5.58, 4.67, 4.56, 4.42, 3.57, 2.37, 1.42; IR (drift) 2959, 2927, 2860, 2815, 1656, 1604, 1555, 1493, 1457, 1409, 1359, 1347, 1322, 1112, 810 cm−1; Specific Rotation (25° C.) αD=16 (c 0.92, DMSO); Anal calcd for C27H28ClN3O4: C, 65.65; H, 5.71; N, 8.51. Found: C, 65.33; H, 5.75; N, 8.53.

Example 8

N-(4-chlorobenzyl)-8-[(3R)-3-hydroxy-1-butynyl]-1-methyl-6-(4-morpholinylmethyl)-4-oxo-1,4-dihydro-3-quinolinecarboxamide

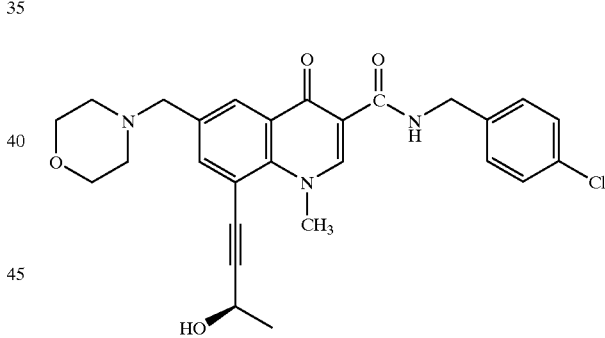

To a solution of N-(4-chlorobenzyl)-8-iodo-1-methyl-6-(4-morpholinylmethyl)-4-oxo-1,4-dihydro-3-quinolinecarboxamide (300 mg), PdCl2(PPh3)2 (19.1 mg), and CuI (5.2 mg) in Et2NH (6.2 mL) is added (S)-(−)-3-butyn-2-ol (0.047 mL). Anhydrous DMF (20 mL) is added to help solubilize the reactants (also requires sonication). Reaction is stirred at room temperature overnight, then condensed. The resulting residue is placed under high vac to remove residual DMF. The crude product is dissolved in CH2Cl2 and partitioned between CH2Cl2 and H2O. The aqueous layer is extracted with CH2Cl2 (2×). The combined organic layers are dried over Na2SO4, filtered, and condensed. The crude product is adsorbed onto silica and chromatographed (eluent 100% CH2Cl2 (1L), 0.5% MeOH in CH2Cl2 (1L), 1.5% MeOH in CH2Cl2 (1L), 2% MeOH in CH2Cl2 (1L), and 2.5% MeOH in CH2Cl2 (2L)).

Product-containing fractions are combined, concentrated, and recrystallized from hot acetonitrile to afford 108.8 mg (41%) of the desired solid as a white solid.

Physical characteristics are as follows: m.p. 147–150° C.; 1H NMR (400 MHz, DMSO-d6) δ 10.28, 8.75, 8.28, 7.83, 7.38, 5.58, 4.67, 4.56, 4.42, 3.58, 2.37, 1.42; IR (drift) 3314, 2972, 2931, 1653, 1604, 1569, 1551, 1493, 1411, 1361, 1350, 1281, 1113, 810, 796 cm−1; MS (ESI) for m/z 494.0 (M+H)+; Specific Rotation (25° C.) αD=−18 (c 0.89, DMSO); Anal calcd for C27H28ClN3O4: C, 65.65; H, 5.71; N, 8.51. Found: C, 66.03; H, 6.03; N, 8.19.

Example 9

N-(4-chlorobenzyl)-1-methyl-6-(4-morpholinylmethyl)-4-oxo-8-{4-[(4R)-2-oxo-1,3-oxazolidin-4-yl]-1-butynyl}-1,4-dihydro-3-quinolinecarboxamide

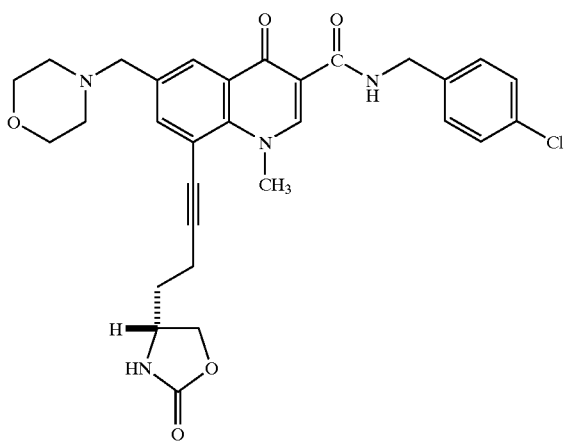

To a solution of N-(4-chlorobenzyl)-8-iodo-1-methyl-6-(4-morpholinylmethyl)-4-oxo-1,4-dihydro-3-quinolinecarboxamide (300 mg), PdCl2(PPh3)2 (19.1 mg), and CuI (5.2 mg) in Et2NH (6.2 mL) is added (4R)-4-(3-butynyl)-1,3-oxazolidin-2-one (83.4 mg). Anhydrous DMF (20 mL) is added to help solubilize the reactants (also requires sonication). The reaction is stirred at room temperature overnight, then condensed. The resulting residue is placed under high vac to remove residual DMF. The crude product is dissolved in CH2Cl2 and partitioned between CH2Cl2 and H2O. The aqueous layer is extracted with CH2Cl2 (2×). The combined organic layers are dried over Na2SO4, filtered, and condensed. The crude product is adsorbed onto silica and chromatographed (eluent 100% CH2Cl2 (1L), 0.5% MeOH in CH2Cl2 (1L), 1% MeOH in CH2Cl2 (1L), 1.5% MeOH in CH2Cl2 (1L), 2% MeOH in CH2Cl2 (1L), and 2.5% MeOH in CH2Cl2 (3L)). Product-containing fractions are combined, concentrated, and recrystallized from hot acetonitrile to afford 95.6 mg (31%) of the desired product as a white solid.

Physical characteristics are as follows: m.p. 171–173° C.; 1H NMR (300 MHz, DMSO-d6) δ 10.28, 8.75, 8.26, 7.92, 7.83, 7.38, 4.55, 4.42, 4.02, 3.92, 3.57, 2.58, 2.36, 1.79; IR (drift) 3218, 1755, 1736, 1655, 1601, 1569, 1551, 1535, 1492, 1361, 1346, 1246, 1114, 807, 798 cm−1; HRMS (FAB) calcd for C30H31ClN4O5+H1 563.2061, found 563.2055; Specific Rotation (25° C.) αD=25 (c 0.96, DMSO).

Example 10

N-(4-chlorobenzyl)-8-(5-hydroxy-1-pentynyl)-1-methyl-6-(4-morpholinylmethyl)-4-oxo-1,4-dihydro-3-quinolinecarboxamide

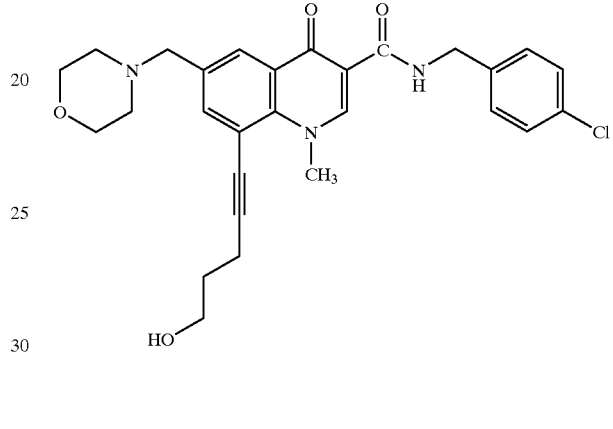

To a solution of N-(4-chlorobenzyl)-8-iodo-1-methyl-6-(4-morpholinylmethyl)-4-oxo-1,4-dihydro-3-quinolinecarboxamide (300 mg), PdCl2 (PPh3)2 (19.1 mg), and CuI (5.2 mg) in Et2NH (6.2 mL) is added 4-pentyn-1-ol (0.056 mL). Anhydrous DMF (20 mL) is added to help solubilize the reactants (also requires sonication). The reaction is stirred at room temperature overnight, then condensed. The resulting residue is placed under high vac to remove residual DMF. The crude product is dissolved in CH2Cl2 and partitioned between CH2Cl2 and H2O. The aqueous layer is extracted with CH2Cl2 (2×). The combined organic layers are dried over Na2SO4, filtered, and condensed. The crude product is adsorbed onto silica and chromatographed (eluent 100% CH2Cl2 (1L), 0.5% MeOH in CH2Cl2 (1L), 1% MeOH in CH2Cl2 (1L), 1.5% MeOH in CH2Cl2 (1L), and 2% MeOH in CH2Cl2 (5L)). Product-containing fractions are combined, concentrated, and recrystallized from hot acetonitrile to afford 117.5 mg (43%) of the desired product as a creme solid.

Physical characteristics are as follows: m.p. 179–182° C.; 1H NMR (300 MHz, DMSO-d6) δ 10.28, 8.74, 8.25, 7.82, 7.38, 4.58, 4.42, 3.57, 3.53, 2.57, 2.37, 1.73; IR (drift) 3042, 2958, 2931, 2861, 2849, 2817, 1656, 1602, 1551, 1491, 1361, 1348, 1118, 809, 798 cm−1; MS (ESI) for m/z 508.0 (M+H)+, 506.0 (M−H)−; Anal calcd for C28H30ClN3O4: C, 66.20; H, 5.95; N, 8.27. Found: C, 66.23; H, 6.08; N, 8.11.

Example 11

N-(4-chlorobenzyl)-8-[3-(1,1-dioxido-4-thiomorpholinyl)-1-propynyl]-1-methyl-6-(4-morpholinylmethyl)-4-oxo-1,4-dihydro-3-quinolinecarboxamide

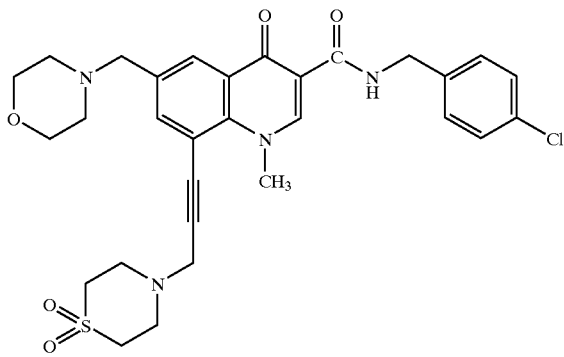

To a solution of N-(4-chlorobenzyl)-8-iodo-1-methyl-6-(4-morpholinylmethyl)-4-oxo-1,4-dihydro-3-quinolinecarboxamide (300 mg), PdCl2(PPh3)2 (19.1 mg), and CuI (5.2 mg) in Et2NH (6.2 mL) is added 4-propargylthiomorpholine-1,1-dioxide (103.8 mg). Anhydrous DMF (18 mL) is added to help solubilize the reactants (also requires sonication). The reaction is stirred at room temperature overnight, then condensed. The resulting residue is placed under high vac to remove residual DMF. The crude product is dissolved in CH2Cl2 and partitioned between CH2Cl2 and H2O. The aqueous layer is extracted with CH2Cl2 (2×). The combined organic layers are dried over Na2SO4, filtered, and condensed. The crude product is adsorbed onto silica and chromatographed (eluent 100% CH2Cl2 (1L), 0.5% MeOH in CH2Cl2 (1L), 1% MeOH in CH2Cl2 (1L), 1.5% MeOH in CH2Cl2 (1L), and 2% MeOH in CH2Cl2 (4L), and 2.5% MeOH in CH2Cl2 (3L)). Product-containing fractions are combined, concentrated, and further purified by HPLC. The product is recrystallized from hot acetonitrile to afford 86.1 mg (27%) of the desired product as a white solid.

Physical characteristics are as follows: m.p. 220–222° C.; 1H NMR (300 MHz, DMSO-d6) δ 10.27, 8.76, 8.30, 7.88, 7.38, 4.56, 4.43, 3.81, 3.59, 3.18, 3.06, 2.37; IR (drift) 1672, 1608, 1563, 1538, 1491, 1359, 1352, 1334, 1310, 1302, 1292, 1273, 1125, 1112, 812 cm−1; MS (ESI) for m/z 596.8 (M+H)+, 594.7 (M−H)−; Anal calcd for C30H33ClN4O5S: C, 60.34; H, 5.57; N, 9.38. Found: C, 60.15; H, 5.62; N, 9.39.

Example 12

N-(4-chlorobenzyl)-8-(3-fluoroprop-1-ynyl)-1-methyl-6-(morpholin-4-ylmethyl)-4-oxo-1,4-dihydroquinoline-3-carboxamide

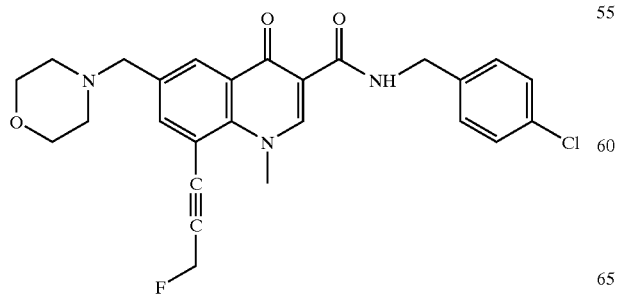

A suspension of propargyl bromide (4.68 mL of an 80 wt % solution in toluene) and KF (12.6 g) in diethylene glycol (19.3 mL) is heated at 56° C. for 5 h in a 100 mL one-necked 14/20 round-bottom flask. This flask is connected to a bulb-to-bulb distillation apparatus. The receiving end of this apparatus is connected to a 50 mL one-necked 14/20 round-bottom flask containing a solution of N-(4-chlorobenzyl)-8-iodo-1-methyl-6-(morpholin-4-ylmethyl)-4-oxo-1,4-dihydroquinoline-3-carboxamide (300 mg), PdCl2(PPh3)2 (19.1 mg), and CuI (5.2 mg) in Et2NH (6.2 mL) and anhydrous DMF (18 mL) cooled to a sub-zero temperature with a dry-ice/acetone bath. After 5 h, the dry-ice/acetone is replaced with ice water to warm the receiving flask to 0° C. The receiving flask is maintained at 0–10° C. for 2.5 h, then allowed to stir at room temperature for 2 days. The reaction mixture is condensed, then further dried under the vacuum pump to remove DMF. The resulting crude solid is dissolved in CH2Cl2 and partitioned against H2O. The layers are separated. The aqueous layer is washed with CH2Cl2 (2×). Organics are combined, dried over Na2SO4, filtered, and condensed to afford a solid. The solid is adsorbed onto silica and chromatographed (eluant 1% MeOH in CH2Cl2 (1L)). Product-containing fractions are combined and condensed to afford a solid consisting of the desired product and starting material. The mixture is separated by HPLC and the desired product is further purified by Biotage flash chromatography (eluant 100% CH2Cl2 (1L) and 1% MeOH in CH2Cl2 (1L)). Product-containing fractions are combined, condensed, and recrystallized from hot acetonitrile to afford 65.2 mg of the title compound as white needles.

Physical characteristics are as follows: m.p. 189–191° C.; 1H NMR (300 MHz, DMSO-d6) δ 10.25, 8.77, 8.34, 7.94, 7.38, 5.52, 5.36, 4.56, 4.41, 3.58, 2.38; IR (diffuse reflectance) 3053, 1662, 1604, 1569, 1551, 1493, 1459, 1409, 1365, 1347, 1124, 1112, 1008, 985, 811 cm−1; HRMS (FAB) calcd for C26H25ClFN3O3+H1 482.1646, found 482.1650; Anal. Calcd for C26H25ClFN3O3: C, 64.79; H, 5.23; N, 8.72. Found: C, 64.58; H, 5.29; N, 8.69.

Example 13

N-(4-chlorobenzyl)-8-[3-(4,5-dichloro-1H-imidazol-1-yl)prop-1-ynyl]-1-methyl-6-(morpholin-4-ylmethyl)-4-oxo-1,4-dihydroquinoline-3-carboxamide

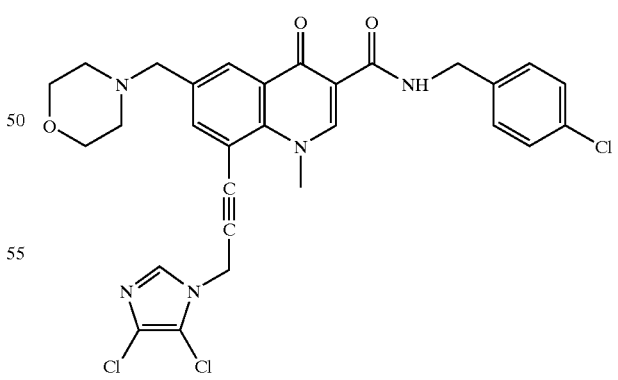

To a suspension of N-(4-chlorobenzyl)-8-iodo-1-methyl-6-(morpholin-4-ylmethyl)-4-oxo-1,4-dihydroquinoline-3-carboxamide (300 mg), PdCl2(PPh3)2 (19.1 mg), and CuI (5.2 mg) in Et2NH (6.2 mL) and anhydrous DMF (10 mL) is added 4,5-dichloro-1-prop-2-ynylimidazole (104.8 mg). The reaction is sonicated and stirred at room temperature for 2 days. The reaction is condensed to afford a residue. The residue is adsorbed onto silica and chromatographed (eluant 100% CH2Cl2 (1L), 0.5% MeOH in CH2Cl2 (1L), 1% MeOH in CH2Cl2 (1L), 1.5% MeOH in CH2Cl2 (1L), and 2% MeOH in CH2Cl2 (3L)). Product-containing fractions are combined and condensed to afford 20 mg of the title compound as a white solid.

Physical characteristics are as follows: m.p. 178–181° C.; 1H NMR (300 MHz, DMSO-d6) δ 10.24, 8.75, 8.32, 8.01, 7.90, 7.38, 5.31, 4.55, 4.35, 3.58, 2.36; IR (diffuse reflectance) 1666, 1608, 1573, 1542, 1491, 1408, 1355, 1248, 1114, 977, 863, 848, 810, 802, 652 cm−1; MS (FAB) m/z 598, 602, 601, 600, 599, 598, 597, 596, 150, 125, 100; Anal. calcd for C29H26Cl3N5O3: C, 58.16; H, 4.38; N, 11.69. Found: C, 58.22; H, 4.49; N, 11.49.

Example 14

N-(4-chlorobenzyl)-1-methyl-8-[3-(5-methyl-1H-imidazol-1-yl)prop-1-ynyl]-6-(morpholin-4-ylmethyl)-4-oxo-1,4-dihydroquinoline-3-carboxamide

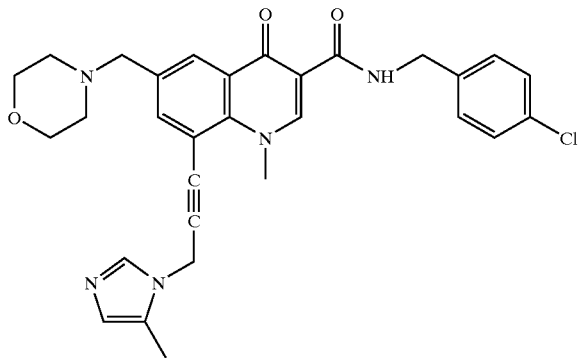

To a solution of N-(4-chlorobenzyl)-8-iodo-1-methyl-6-(morpholin-4-ylmethyl)-4-oxo-1,4-dihydroquinoline-3-carboxamide (300 mg), PdCl2(PPh3)2 (19.1 mg), and CuI (5.2 mg) in Et2NH (6.2 mL) is added 5-methyl-1-prop-2-ynyl-1H-imidazole hydrobromide (120.4 mg). Anhydrous DMF (10 mL) is added to help solubilize the reactants (also requires sonication). The reaction is stirred at room temperature overnight, then condensed. The resulting residue is placed under high vacuum to remove residual DMF. The crude product is dissolved in CH2Cl2 and partitioned between CH2Cl2 and saturated NaHCO3. The layers are separated. The aqueous layer is extracted with CH2Cl2 (2×). The combined organic layers are dried over Na2SO4, filtered, and condensed. The crude product is adsorbed onto silica and chromatographed (eluant 1% MeOH in CH2Cl2 (1L), 2% MeOH in CH2Cl2 (1L), 3% MeOH in CH2Cl2 (1L), 4% MeOH in CH2Cl2 (2L), and 6% MeOH in CH2Cl2 (1L)). Product-containing fractions are combined and concentrated to afford a residue. The residue is recrystallized from hot acetonitrile to afford 87.7 mg of the title compound as a tan solid.

Physical characteristics are as follows: m.p. 149–152° C.; 1H NMR (300 MHz, DMSO-d6) δ 10.25, 8.74, 8.30, 7.87, 7.71, 7.37, 6.72, 5.20, 4.55, 4.32, 3.57, 2.36, 2.29.

Example 15

N-(4-chlorobenzyl)-1-methyl-6-(morpholin-4-ylmethyl)-4-oxo-8-(pyridin-2-ylethynyl)-1,4-dihydroquinoline-3-carboxamide

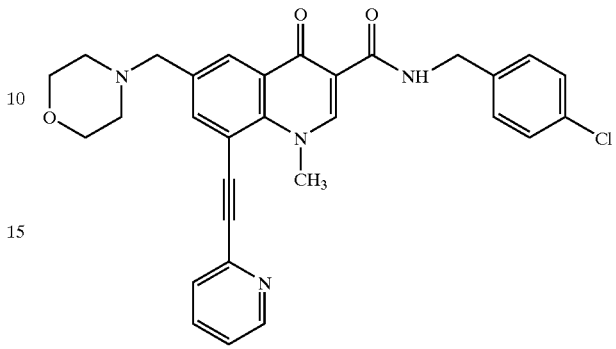

A flame-dried flask under an atmosphere of nitrogen gas containing N-(4-chlorobenzyl)-8-iodo-1-methyl-6-(morpholin-4-ylmethyl)-4-oxo-1,4-dihydroquinoline-3-carboxamide (Preparation # 15) (0.28 g) is treated with copper (I) iodide (0.01 g), dichlorobis(triphenylphosphine) palladium (II) (0.03 g), dimethylformamide (DMF) (3 mL) and diethylamine (3 mL). The resulting stirring suspension is treated with 2-ethynylpyridine (0.1 mL). After stirring overnight, the suspension is concentrated under reduced pressure and then in vacuo. The residue is adsorbed onto silica gel and is flash column chromatographed on silica eluting with 2% to 6% methanol in dichloromethane. The product-containing fractions are combined and concentrated under reduced pressure. The resulting material is crystallized from a mixture of methanol:acetonitrile to afford the title compound (0.22 g) as a white solid.

Physical characteristics are as follows: m.p. 234–236° C.; 1H NMR (d6-DMSO) δ 10.3, 8.8, 8.7, 8.4, 8.1, 7.9, 7.7, 7.5, 7.4, 4.6, 3.6, 2.4; HRMS (FAB) calc'd for C30H27ClN4O3+H1 527.1850, found 527.1858; anal. calc'd for C30H27ClN4O3: C, 68.37; H, 5.16; N, 10.63; found: C, 68.14; H, 5.17; N, 10.53.

Example 16

N-(4-chlorobenzyl)-1-methyl-6-(morpholin-4-ylmethyl)-4-oxo-8-(pyridin-3-ylethynyl)-1,4-dihydroquinoline-3-carboxamide

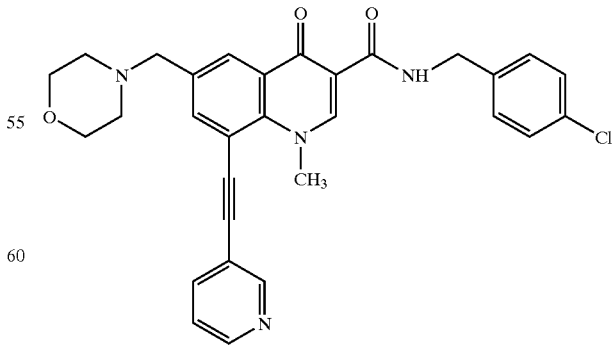

A flame-dried flask under an atmosphere of nitrogen gas containing N-(4-chlorobenzyl)-8-iodo-1-methyl-6-

(morpholin-4-ylmethyl)-4-oxo-1,4-dihydroquinoline-3-carboxamide (Preparation # 15) (0.28 g) is treated with copper (I) iodide (0.01 g), dichlorobis(triphenylphosphine) palladium (II) (0.03 g) and 3-ethynylpyridine (0.10 g). The solids are treated with dimethylformamide (DMF) (3 mL) and diethylamine (3 mL). The resulting suspension is stirred for 2 days and is then concentrated under reduced pressure. The residue is flash column chromatographed on silica eluting with 2% to 4% methanol in dichloromethane. The product-containing fractions are combined and concentrated under reduced pressure. The resulting material is crystallized from methanol:acetonitrile to afford the title compound (0.23 g) as a tan solid.

Physical characteristics are as follows: m.p. 195–197° C.; 1H NMR (d6-DMSO) δ 10.3, 8.8, 8.8, 8.6, 8.3, 8.1, 8.0, 7.5, 7.4, 4.6, 4.5, 3.6, 2.4; HRMS (FAB) calc'd for C30H27ClN4O3+H1 527.1850, found 527.1851; anal. calc'd for C30H27ClN4O3: C, 68.37; H, 5.16; N, 10.63; found: C, 67.99; H, 5.20; N, 10.53.

Example 17

N-(4-chlorobenzyl)-1-methyl-6-(morpholin-4-ylmethyl)-4-oxo-8-(pyridin-4-ylethynyl)-1,4-dihydroquinoline-3-carboxamide

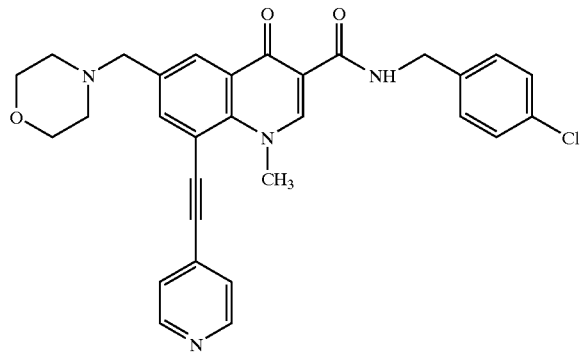

A flame-dried flask under an atmosphere of nitrogen gas containing N-(4-chlorobenzyl)-8-iodo-1-methyl-6-(morpholin-4-ylmethyl)-4-oxo-1,4-dihydroquinoline-3-carboxamide (Preparation # 15) (0.28 g) is treated with copper (I) iodide (0.01 g), dichlorobis(triphenylphosphine) palladium (II) (0.03 g) and 3-ethynylpyridine (0.10 g). The solids are treated with dimethylformamide (DMF) (3 mL) and diethylamine (3 mL). The resulting suspension is stirred overnight, concentrated under reduced pressure and finally in vacuo. The residue is flash column chromatographed on silica eluting with 2% to 6% methanol in dichloromethane. The product-containing fractions are combined and concentrated under reduced pressure. The resulting material is crystallized from acetonitrile to afford the title compound (0.23 g) as light yellow needles.

Physical characteristics are as follows: m.p. 200–202° C.; 1H NMR (d6-DMSO) δ 10.3, 8.8, 8.7, 8.4, 8.1, 7.6, 7.4, 4.6, 4.5, 3.6, 2.4; HRMS (FAB) calc'd for C30H27ClN4O3+H1 527.1850, found 527.1838; anal. calc'd for C30H27ClN4O3: C, 68.37; H, 5.16; N, 10.63; found: C, 68.08; H, 5.15; N, 10.54.

Example 18

N-(4-chlorobenzyl)-8-(4-hydroxypent-1-ynyl)-1-methyl-6-(morpholin-4-ylmethyl)-4-oxo-1,4-dihydroquinoline-3-carboxamide

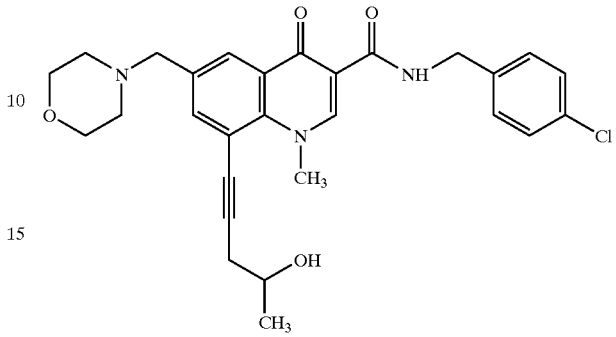

A flame-dried flask under an atmosphere of nitrogen gas containing N-(4-chlorobenzyl)-8-iodo-1-methyl-6-(morpholin-4-ylmethyl)-4-oxo-1,4-dihydroquinoline-3-carboxamide (Preparation # 15) (0.55 g) is treated with copper (I) iodide (0.02 g) and dichlorobis(triphenylphosphine)palladium (II) (0.07 g). The solids are treated with dimethylformamide (DMF) (6 mL) and diethylamine (6 mL). The resulting suspension is treated with 4-pentyn-2-ol (0.2 mL) and stirred for 4 days. The reaction is concentrated under reduced pressure and the residue is partitioned between ethyl acetate and phosphate buffer (pH=7). The aqueous phase is extracted with dichloromethane:ethyl acetate. The combined organic layers are washed with phosphate buffer (pH=7), brine, dried (Na2SO4), filtered and concentrated under reduced pressure. The residue is flash column chromatographed on silica eluting with 5% to 11% methanol in ethyl acetate. The product-containing fractions are combined and concentrated under reduced pressure. The resulting material is crystallized from acetonitrile:methanol and then re-crystallized from toluene to afford the title compound (0.33 g) as off-white solid.

Physical characteristics are as follows: m.p. 178–180° C.; 1H NMR (d6-DMSO) δ10.3, 8.7, 8.2, 7.8, 7.4, 4.9, 4.5, 4.4, 3.9, 3.6, 2.6, 2.3, 1.2; anal. calc'd for C28H30ClN3O4: C, 66.20; H, 5.95; N, 8.27; found: C, 66.06; H, 6.05; N, 8.20.

Example 19

N-(4-chlorobenzyl)-8-[3-(4-hydroxypiperidin-1-yl)prop-1-ynyl]-1-methyl-6-(morpholin-4-ylmethyl)-4-oxo-1,4-dihydroquinoline-3-carboxamide

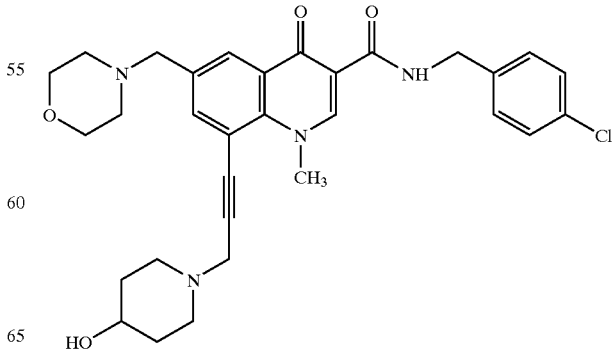

A mixture of N-(4-chlorobenzyl)-8-(3-hydroxy-1-propynyl)-1-methyl-6-(4-morpholinylmethyl)-4-oxo-1,4-dihydro-3-quinolinecarboxamide (0.14 g) in dichloromethane (3 mL) is treated with triphenylphosphine (0.15 g) and carbon tetrabromide (0.18 g). The reaction is stirred overnight. The resulting suspension is treated with additional triphenylphosphine (0.03 g) and carbon tetrabromide (0.03 g). After 4 hrs, the mixture is adsorbed onto silica, concentrated under reduced pressure and flash column chromatographed eluting with 3% methanol in dichloromethane to provide the crude propargylic bromide contaminated with triphenylphosphine oxide.

The crude bromide is dissolved in dichloromethane (5 mL) and is treated with 4-hydroxypiperidine (0.24 g). After 3 days, the reaction mixture is diluted ethyl acetate (100 mL) and is washed with pH=7 phosphate buffer (2×50 mL), brine, dried (Na2SO4), filtered and concentrated under reduced pressure. The residue is flash column chromatographed on silica gel eluting with 4% to 20% methanol in dichloromethane. The product-containing fractions are concentrated under reduced pressure and the resulting residue is crystallized from methanol:acetonitrile to afford the title compound (0.12 g) as a pale yellow solid.

Physical characteristics are as follows: m.p. 180–183° C.; 1H NMR (d6-DMSO) δ10.3, 8.7, 8.3, 7.9, 7.4, 4.6, 4.6, 4.4, 3.6, 3.5, 2.8, 2.4, 2.3, 1.8, 1.45; HRMS (FAB) calc'd for C31H35ClN4O4+H1 563.2425, found 563.2435; anal. calc'd for C31H35ClN4O4: C, 66.12; H, 6.26; N, 9.95; found: C, 65.76; H, 6.27; N, 9.96.

Example 20

N-(4-chlorobenzyl)-8-[3-(3-hydroxypyrrolidin-1-yl)prop-1-ynyl]-1-methyl-6-(morpholin-4-ylmethyl)-4-oxo-1,4-dihydroquinoline-3-carboxamide

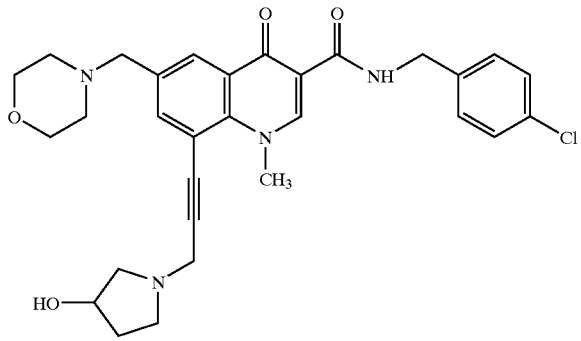

A mixture of N-(4-chlorobenzyl)-8-(3-hydroxy-1-propynyl)-1-methyl-6-(4-morpholinylmethyl)-4-oxo-1,4-dihydro-3-quinolinecarboxamide (0.55 g) in dichloromethane (10 mL) is treated with triphenylphosphine (0.62 g) and carbon tetrabromide (0.77 g). After stirring overnight, the reaction mixture is adsorbed onto silica, concentrated under reduced pressure and flash column chromatographed eluting with 1% to 3% methanol in dichloromethane to provide the crude propargylic bromide contaminated with triphenylphosphine oxide. Half of the crude bromide is added to dichloromethane (5 mL) and is treated with 3-pyrrolidinol (0.21 mL). After 4 days, the reaction mixture is diluted ethyl acetate:dichloromethane and is washed with pH=7 phosphate buffer, brine, dried (Na2SO4), filtered and concentrated under reduced pressure. The residue is flash column chromatographed on silica gel eluting with 5% to 15% methanol in dichloromethane. The product-containing fractions are concentrated under reduced pressure and the resulting residue is crystallized from acetonitrile to afford the title compound (0.08 g) as a light yellow solid.

Physical characteristics are as follows: m.p. 144–146° C.; 1H NMR (d6-DMSO) δ 10.3, 8.7, 8.3, 7.9, 7.4, 4.8, 4.5, 4.4, 4.2, 3.7, 3.6, 2.9, 2.8, 2.6, 2.5, 2.4, 2.0, 1.6; HRMS (FAB) calc'd for C30H33ClN4O4+H1 549.2268, found 549.2252.

Example 21

N-(4-chlorobenzyl)-8-{3-[(2,3-dihydroxypropyl)(methyl)amino]prop-1-ynyl}-1-methyl-6-(morpholin-4-ylmethyl)-4-oxo-1,4-dihydroquinoline-3-carboxamide

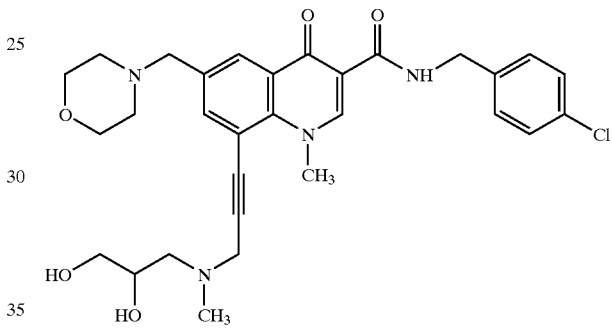

A mixture of N-(4-chlorobenzyl)-8-(3-hydroxy-1-propynyl)-1-methyl-6-(4-morpholinylmethyl)-4-oxo-1,4-dihydro-3-quinolinecarboxamide (0.39 g) in dichloromethane (4 mL) is treated with triphenylphosphine (0.42 g) and carbon tetrabromide (0.53 g). After stirring overnight, the reaction mixture is adsorbed onto silica, concentrated under reduced pressure and flash column chromatographed eluting with 2% methanol in dichloromethane to provide the crude propargylic bromide contaminated with triphenylphosphine oxide. The crude bromide is added to dichloromethane (2 mL) and is treated with 3-methylamino-1,2-propanediol (0.16 g). After 2 days, the reaction mixture is added to ethyl acetate and is washed with pH=7 phosphate buffer. The organic phase is treated with dichloromethane:methanol and is washed with pH=7 phosphate buffer, brine, dried (Na2SO4), filtered and concentrated under reduced pressure. The residue is flash column chromatographed on silica gel eluting with 5% to 20% methanol in dichloromethane. The product-containing fractions are concentrated under reduced pressure and the resulting residue is crystallized from acetonitrile to afford the title compound (0.08 g) as a light yellow solid.

Physical characteristics are as follows: m.p. 140–142° C.; 1H NMR (d6-DMSO) δ10.3, 8.7, 8.3, 7.9, 7.4, 4.6–4.5, 4.4, 3.7, 3.6, 2.5, 2.4; HRMS (FAB) calc'd for C30H35ClN4O5+H1 567.2374, found 567.2369

Example 22

N-(4-chlorobenzyl)-8-{3-[(2-hydroxyethyl)(methyl)amino]prop-1-ynyl}-1-methyl-6-(morpholin-4-ylmethyl)-4-oxo-1,4-dihydroquinoline-3-carboxamide

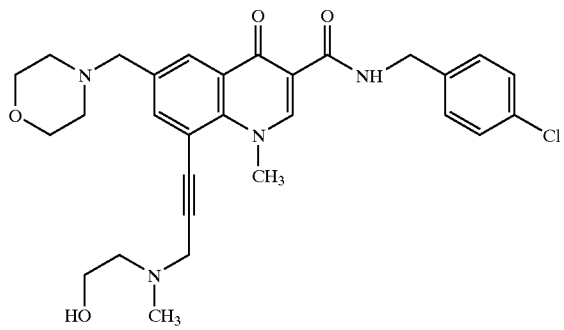

A mixture of N-(4-chlorobenzyl)-8-(3-hydroxy-1-propynyl)-1-methyl-6-(4-morpholinylmethyl)-4-oxo-1,4-dihydro-3-quinolinecarboxamide (0.24 g) in dichloromethane (4 mL) is treated with polymer bound triphenylphosphine (3 mmol/g, 0.50 g) and carbon tetrabromide (0.33 g). After shaking overnight, the reaction mixture is filtered and the resin washed with dichloromethane (3×10 mL). The filtrate is concentrated under reduced pressure and the resulting residue flash column chromatographed eluting with 2% methanol in dichloromethane to provide the crude propargylic bromide. The crude bromide is added to dichloromethane (4 mL) and is treated with N-methyl ethanolamine (0.03 mL) and polymer bound trimethylammonium carbonate (3.5 eq/g, 0.4 g). After shaking overnight, the reaction is treated with polymer bound isocyanate resin (1.25 eq/g, 0.5 g). After 4 days, the reaction mixture is filtered and the resin is washed with dichloromethane (4×10 mL). The filtrates are combined and concentrated under reduced pressure. The residue is flash column chromatographed on silica gel eluting with 5% to 20% methanol in dichloromethane. The product-containing fractions are concentrated under reduced pressure and the resulting residue is crystallized from acetonitrile to afford the title compound (0.09 g) as a light yellow solid.

Physical characteristics are as follows: m.p. 148–149° C.; 1H NMR (d6-DMSO) δ10.3, 8.7, 8.3, 7.9, 7.4, 4.6, 4.5, 4.4, 3.7, 3.6, 3.5, 2.6, 2.4, 2.3; HRMS (FAB) calc'd for C29H33ClN4O4+H1 537.2268, found 537.2267; anal. calc'd for C29H33ClN4O4: C, 64.86; H, 6.19; N, 10.43; found: C, 64.57; H, 6.16; N, 10.46.

Example 23

N-(4-chlorobenzyl)-8-[3-(1H-imidazol-1-yl)prop-1-ynyl]-1-methyl-6-(morpholin-4-ylmethyl)-4-oxo-1,4-dihydroquinoline-3-carboxamide

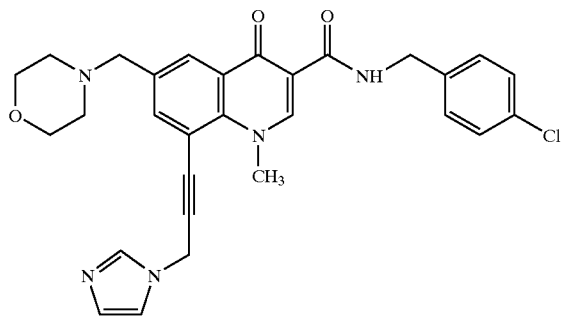

A mixture of N-(4-chlorobenzyl)-8-(3-hydroxy-1-propynyl)-1-methyl-6-(4-morpholinylmethyl)-4-oxo-1,4-dihydro-3-quinolinecarboxamide (0.48 g) in dichloromethane (20 mL) is treated with polymer bound triphenylphosphine (3 mmol/g, 1.0 g) and carbon tetrabromide (0.65 g). After shaking overnight, the reaction mixture is filtered and the resin washed with dichloromethane (3×20 mL). The combined filtrate is concentrated under reduced pressure and in vacuo. The resulting crude bromide is added to dichloromethane (3 mL) and is treated with imidazole (0.11 g). After stirring for 2 days, the reaction is diluted with dichloromethane and washed with pH=7 phosphate buffer, brine, dried (Na2SO4), filtered and concentrated under reduced pressure. The residue is flash column chromatographed on silica gel eluting with 2% to 9% methanol in dichloromethane. The product-containing fractions are concentrated under reduced pressure and the resulting residue is crystallized from acetonitrile to afford the title compound (0.08 g) as a white solid.

Physical characteristics are as follows: m.p. 178–180° C.; 1H NMR (d6-DMSO) δ10.2, 8.7, 8.3, 7.9, 7.8, 7.4, 7.3, 7.0, 5.3, 4.5, 4.3, 3.6, 2.3; HRMS (FAB) calc'd for C29H28ClN5O3+H1 530.1959, found 530.1967; anal. calc'd for C29H28ClN5O3: C, 65.72; H, 5.32; N, 13.21; Cl, 6.69; found: C, 65.50; H, 5.41; N, 13.17.

Example 24

N-(4-chlorobenzyl)-8-[5-hydroxy-4-(hydroxymethyl)pent-1-ynyl]-1-methyl-6-(morpholin-4-ylmethyl)-4-oxo-1,4-dihydroquinoline-3-carboxamide

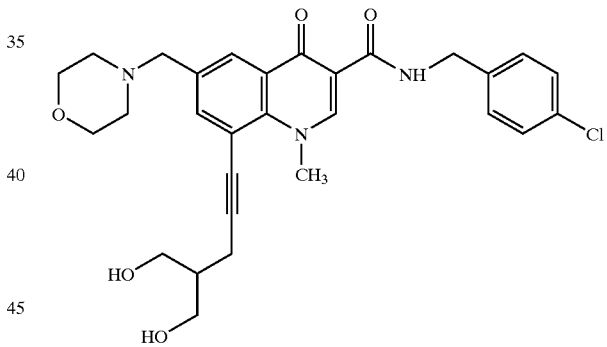

A flame-dried flask under an atmosphere of nitrogen gas containing N-(4-chlorobenzyl)-8-iodo-1-methyl-6-(morpholin-4-ylmethyl)-4-oxo-1,4-dihydroquinoline-3-carboxamide (Preparation # 15) (0.55 g) is treated with 2,2,10,10-tetramethyl-3,3,9,9-tetraphenyl-6-prop-2-ynyl-4,8-dioxa-3,9-disilaundecane (Bioorg. Med. Chem. Lett. 1996, 467) (1.4 g), copper (I) iodide (0.02 g) and dichlorobis(triphenylphosphine)palladium (II) (0.07 g). The solids are treated with dimethylformamide (DMF) (10 mL) and diethylamine (10 mL). The resulting suspension is stirred for 4 days and then concentrated under reduced pressure. The residue is partitioned between dichloromethane and phosphate buffer (pH=7). The organic layer is washed with brine, dried (Na2SO4), filtered and concentrated under reduced pressure. The residue is flash column chromatographed on silica eluting with 2% to 4% methanol in dichloromethane. The product-containing fractions are combined and concentrated under reduced pressure to afford the protected diol (0.80 g) as a tan foam. The foam is added as a solution in diethyl ether (10 mL) to a flame-dried flask under an atmosphere of nitrogen gas containing a mixture of acetyl chloride (1.0 mL) in methanol (30 mL) at 0° C. After slowly warming to room temperature over 4 hours, the reaction mixture is slowly poured into vigorously stirred dichloromethane (50 mL) containing sodium bicarbonate (10 g). After about 10 minutes, the reaction is filtered and the filter cake is washed repeatedly with dichloromethane. The combined filtrate is concentrated under reduced pressure. The residue is flash column chromatographed on silica eluting with 2% to 12% methanol in dichloromethane. The product-containing fractions are combined and concentrated under reduced pressure. The residue is crystallized from methanol:acetonitrile to afford the title compound (0.08 g) as a white solid.

Physical characteristics are as follows: m.p. 190–193° C.; 1H NMR (d6-DMSO) δ10.3, 8.7, 8.3, 7.8, 7.4, 4.6, 4.4, 3.6, 3.5, 2.6, 2.4, 1.9; HRMS (FAB) calc'd for C29H32ClN3O5+H1 538.2108, found 538.2114; anal. calc'd for C29H32ClN3O5: C, 64.74; H, 5.99; N, 7.81; found: C, 64.41; H, 6.05; N, 7.87.

Example 25

N-(4-chlorobenzyl)-8-{3-[3-(hydroxymethyl) piperidin-1-yl]prop-1-ynyl}-1-methyl-6-(morpholin-4-ylmethyl)-4-oxo-1,4-dihydroquinoline-3-carboxamide

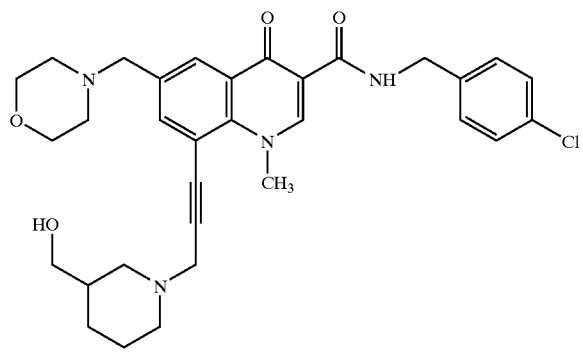

A mixture of N-(4-chlorobenzyl)-8-(3-hydroxy-1-propynyl)-1-methyl-6-(4-morpholinylmethyl)-4-oxo-1,4-dihydro-3-quinolinecarboxamide (0.24 g) and dry lithium chloride (0.10 g) in dichloromethane (10 mL) under a drying tube at 0° C. is treated with triethylamine (0.20 mL) and mesyl chloride (0.10 mL). After slowly warming to room temperature overnight, the reaction mixture is diluted with dichloromethane, washed with pH=7 phosphate buffer, brine, dried (Na2SO4), filtered and concentrated under reduced pressure. The resulting residue is dissolved in dichloromethane (10 mL). Half of the dichloromethane mixture (5 mL) is treated with 3-piperdininemethanol (0.12 g). After shaking for 4 days, the reaction is diluted with dichloromethane (10 mL) and is treated with polymer-bound isocyanate resin (1.25 eq/g, 1.0 g). After shaking for 2 days, the reaction is filtered, the resin is washed with dichloromethane (3×20 mL), and the combined filtrates are concentrated under reduced pressure. The residue is dissolved in dichloromethane and is washed with phosphate buffer (pH=7), brine, dried (Na2SO4), filtered and concentrated under reduced pressure. The residue is crystallized from acetonitrile to afford the title compound as a white solid.

Physical characteristics are as follows: 1H NMR (d6-DMSO) δ10.3, 8.7, 8.3, 7.9, 7.4, 4.6, 4.5, 4.4, 3.6, 3.3, 2.9, 2.8, 2.4, 2.2, 1.9, 1.6, 1.5, 0.9; HRMS (FAB) calc'd for C32H37ClN4O4+H1 577.2581, found 577.2590.

Example 26

N-(4-chlorobenzyl)-8-{3-[4-(2-hydroxyethyl) piperazin-1-yl]prop-1-ynyl}-1-methyl-6-(morpholin-4-ylmethyl)-4-oxo-1,4-dihydroquinoline-3-carboxamide

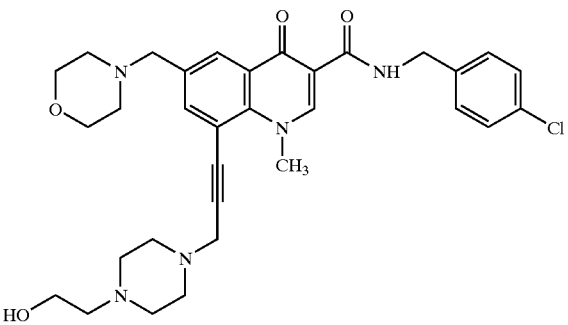

A mixture of N-(4-chlorobenzyl)-8-(3-hydroxy-1-propynyl)-1-methyl-6-(4-morpholinylmethyl)-4-oxo-1,4-dihydro-3-quinolinecarboxamide (0.24 g) in dichloromethane (10 mL) under a drying tube is treated with triethylamine (0.10 mL) and mesyl chloride (0.05 mL) at 0° C. After slowly warming to room temperature overnight, the reaction mixture is treated with triethylamine (0.05 mL) and mesyl chloride (0.03 mL) and stirred overnight. The reaction mixture is diluted with dichloromethane and washed with pH=7 phosphate buffer. The aqueous phase is extracted with dichloromethane and the combined organic layer is washed with brine, dried (Na2SO4), filtered and concentrated under reduced pressure. The resulting residue is dissolved in dichloromethane (10 mL). Half of the dichloromethane mixture (5 mL) is treated with 1-(2-hydroxyethyl)piperazine (0.13 mL). After shaking for 5 days, the reaction is diluted with dichloromethane (40 mL) and is partitioned against phosphate buffer (pH=7, 20 mL). The aqueous phase is extracted with dichloromethane (20 mL) and the combined organic layer is washed with brine, dried (Na2SO4), filtered and concentrated under reduced pressure. The residue is crystallized from acetonitrile to afford the title compound as a tan solid.

Physical characteristics are as follows: 1H NMR (d6-DMSO) δ10.3, 8.7, 8.3, 7.9, 7.4, 4.6, 4.4, 3.6, 3.5, 2.6, 2.5, 2.4; MS (ESI) for m/z 592 (M+H)+.

Example 27

N-(4-chlorobenzyl)-8-{3-[(2S)-2-(hydroxymethyl) pyrrolidin-1-yl]prop-1-ynyl}-1-methyl-6-(morpholin-4-ylmethyl)-4-oxo-1,4-dihydroquinoline-3-carboxamide

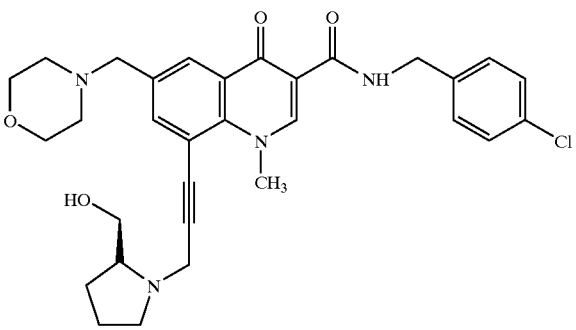

A mixture of N-(4-chlorobenzyl)-8-(3-hydroxy-1-propynyl)-1-methyl-6-(4-morpholinylmethyl)-4-oxo-1,4-dihydro-3-quinolinecarboxamide (3.11 g) in dichloromethane (50 mL) under a drying tube is treated with triethylamine (2.0 mL) and mesyl chloride (1.0 mL). After stirring at room temperature overnight, the reaction mixture is diluted with dichloromethane (100 mL) and partitioned against pH=7 phosphate buffer (100 mL). The aqueous phase is extracted with dichloromethane (50 mL) and the combined organic layer is washed with brine, dried (Na2SO4), filtered and concentrated under reduced pressure. The resulting residue (3.0 g) is treated with dichloromethane (80 mL). An aliquot (2 mL) of the dichloromethane mixture is transferred to a vial and treated with L-pyrolinol (0.06 mL). After shaking for 2 days, the reaction is diluted with diethyl ether:dichloromethane (4:1, 50 mL) and washed with phosphate buffer (pH=7, 15 mL), brine, dried (Na2SO4), filtered and concentrated under reduced pressure. The residue is crystallized from acetonitrile to afford the title compound as a solid.

Physical characteristics are as follows: 1H NMR (d6-DMSO) δ10.3, 8.7, 8.3, 7.9, 7.4, 4.6, 4.4, 3.8, 3.6, 3.4, 3.3, 3.0, 2.7, 2.6, 2.4, 1.9, 1.7, 1.55; MS (ESI) for m/z 563 (M+H)+.

Example 28

N-(4-chlorobenzyl)-8-[3-(3-hydroxypiperidin-1-yl)prop-1-ynyl]-1-methyl-6-(morpholin-4-ylmethyl)-4-oxo-1,4-dihydroquinoline-3-carboxamide

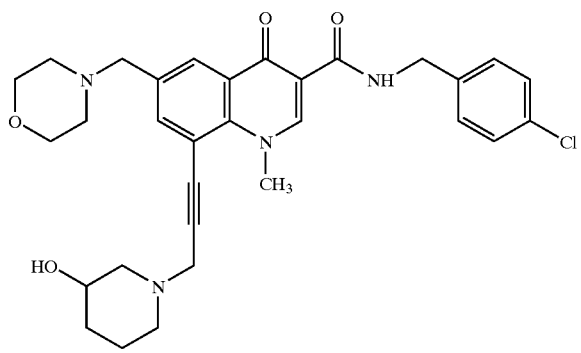

A mixture of N-(4-chlorobenzyl)-8-(3-hydroxy-1-propynyl)-1-methyl-6-(4-morpholinylmethyl)-4-oxo-1,4-dihydro-3-quinolinecarboxamide (3.11 g) in dichloromethane (50 mL) under a drying tube is treated with triethylamine (2.0 mL) and mesyl chloride (1.0 mL). After stirring at room temperature overnight, the reaction mixture is diluted with dichloromethane (100 mL) and partitioned against pH=7 phosphate buffer (100 mL). The aqueous phase is extracted with dichloromethane (50 mL) and the combined organic layer is washed with brine, dried (Na2SO4), filtered and concentrated under reduced pressure. The resulting residue (3.0 g) is treated with dichloromethane (80 mL). An aliquot (2 mL) of the dichloromethane mixture is transferred to a vial and treated with 3-hydroxypiperidine (0.05 g). After shaking for 2 days, the reaction is diluted with diethyl ether:dichloromethane (4:1, 50 mL) and washed with phosphate buffer (pH=7, 15 mL), brine, dried (Na2SO4), filtered and concentrated under reduced pressure. The residue is crystallized from acetonitrile to afford the title compound as a solid.

Physical characteristics are as follows: 1H NMR (d6-DMSO) δ10.3, 8.7, 8.3, 7.9, 7.4, 4.7, 4.6, 4.3, 3.6, 3.5, 2.9, 2.75, 2.4, 2.2, 2.1, 1.8, 1.7, 1.5, 1.1; MS (ESI) for m/z 563 (M+H)+.

Example 29

N-(4-chlorobenzyl)-8-{3-[(2R)-2-(hydroxymethyl)pyrrolidin-1-yl]prop-1-ynyl}-1-methyl-6-(morpholin-4-ylmethyl)-4-oxo-1,4-dihydroquinoline-3-carboxamide

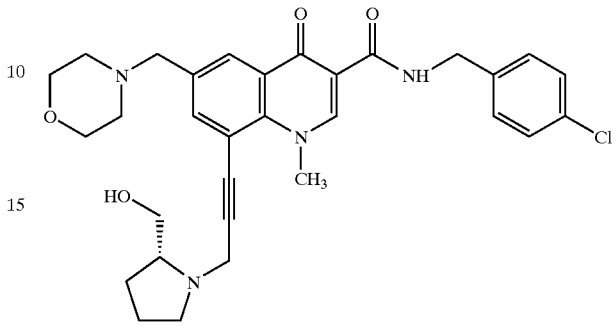

A mixture of N-(4-chlorobenzyl)-8-(3-hydroxy-1-propynyl)-1-methyl-6-(4-morpholinylmethyl)-4-oxo-1,4-dihydro-3-quinolinecarboxamide (3.11 g) in dichloromethane (50 mL) under a drying tube is treated with triethylamine (2.0 mL) and mesyl chloride (1.0 mL). After stirring at room temperature overnight, the reaction mixture is diluted with dichloromethane (100 mL) and partitioned against pH=7 phosphate buffer (100 mL). The aqueous phase is extracted with dichloromethane (50 mL) and the combined organic layer is washed with brine, dried (Na2SO4), filtered and concentrated under reduced pressure. The resulting residue (3.0 g) is treated with dichloromethane (80 mL). An aliquot (2 mL) of the dichloromethane mixture is transferred to a vial and treated with D-pyrolinol (0.06 mL). After shaking for 2 days, the reaction is diluted with diethyl ether:dichloromethane (4:1, 50 mL) and washed with phosphate buffer (pH=7, 15 mL), brine, dried (Na2SO4), filtered and concentrated under reduced pressure. The residue is crystallized from acetonitrile to afford the title compound as a solid.

Physical characteristics are as follows: 1H NMR (d6-DMSO) δ10.3, 8.7, 8.3, 7.9, 7.4, 4.6, 4.4, 3.8, 3.6, 3.4, 3.0, 2.7, 2.6, 2.4, 1.85, 1.7, 1.6; MS (ESI) for m/z 563 (M+H)+.

Example 30

N-(4-chlorobenzyl)-8-{3-[2-(2-hydroxyethyl)piperidin-1-yl]prop-1-ynyl}-1-methyl-6-(morpholin-4-ylmethyl)-4-oxo-1,4-dihydroquinoline-3-carboxamide

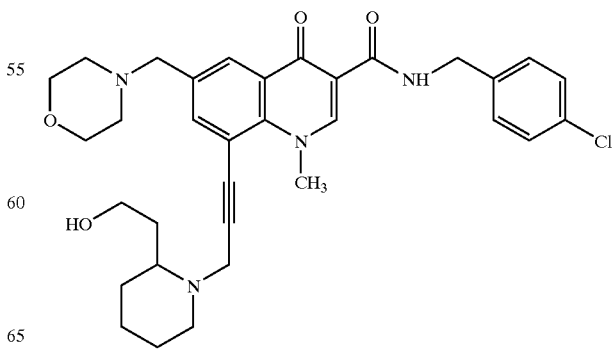

A mixture of N-(4-chlorobenzyl)-8-(3-hydroxy-1-propynyl)-1-methyl-6-(4-morpholinylmethyl)-4-oxo-1,4-dihydro-3-quinolinecarboxamide (3.11 g) in dichloromethane (50 mL) under a drying tube is treated with triethylamine (2.0 mL) and mesyl chloride (1.0 mL). After stirring at room temperature overnight, the reaction mixture is diluted with dichloromethane (100 mL) and partitioned against pH=7 phosphate buffer (100 mL). The aqueous phase is extracted with dichloromethane (50 mL) and the combined organic layer is washed with brine, dried (Na2SO4), filtered and concentrated under reduced pressure. The resulting residue (3.0 g) is treated with dichloromethane (80 mL). An aliquot (2 mL) of the dichloromethane mixture is transferred to a vial and treated with 2-piperidineethanol (0.07 g). After shaking for 2 days, the reaction is treated with sodium iodide (20 mg). After shaking overnight, the reaction is diluted with acetonitrile (1 mL). After shaking overnight, the reaction is diluted with diethyl ether:dichloromethane (4:1, 50 mL) and washed with phosphate buffer (pH=7, 15 mL), brine, dried (Na2SO4), filtered and concentrated under reduced pressure. The residue is crystallized from acetonitrile to afford the title compound as a solid.

Physical characteristics are as follows: 1H NMR (d6-DMSO) δ10.3, 8.7, 8.3, 7.9, 7.4, 4.6, 4.5, 4.4, 3.8, 3.6, 3.5, 2.8, 2.5, 2.4, 1.8, 1.7–1.4, 1.2; MS (ESI) for m/z 591 (M+H)+.

Example 31

8-{3-[butyl(2-hydroxyethyl)amino]prop-1-ynyl}-N-(4-chlorobenzyl)-1-methyl-6-(morpholin-4-ylmethyl)-4-oxo-1,4-dihydroquinoline-3-carboxamide

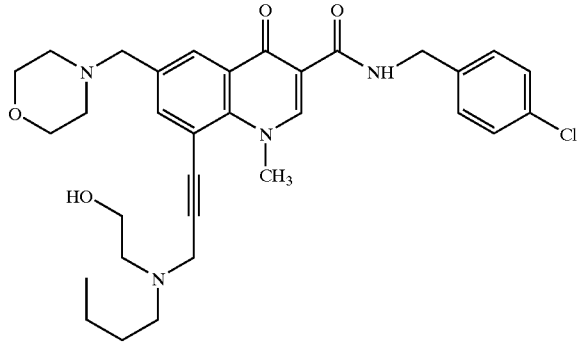

A mixture of N-(4-chlorobenzyl)-8-(3-hydroxy-1-propynyl)-1-methyl-6-(4-morpholinylmethyl)-4-oxo-1,4-dihydro-3-quinolinecarboxamide (3.11 g) in dichloromethane (50 mL) under a drying tube is treated with triethylamine (2.0 mL) and mesyl chloride (1.0 mL). After stirring at room temperature overnight, the reaction mixture is diluted with dichloromethane (100 mL) and partitioned against pH=7 phosphate buffer (100 mL). The aqueous phase is extracted with dichloromethane (50 mL) and the combined organic layer is washed with brine, dried (Na2SO4), filtered and concentrated under reduced pressure. The resulting residue (3.0 g) is treated with dichloromethane (80 mL). An aliquot (2 mL) of the dichloromethane mixture is transferred to a vial and treated with 2-(butylamino)ethanol (0.07 mL). After shaking for 2 days, the reaction is diluted with diethyl ether:dichloromethane (4:1, 50 mL) and washed with phosphate buffer (pH=7, 15 mL), brine, dried (Na2SO4), filtered and concentrated under reduced pressure. The residue is crystallized from acetonitrile to afford the title compound as a solid.

Physical characteristics are as follows: 1H NMR (d6-DMSO) δ10.3, 8.7, 8.3, 7.9, 7.4, 4.6, 4.5, 4.4, 3.7, 3.6, 3.5, 2.6, 2.4, 1.5–1.2, 0.9; MS (ESI) for m/z 579 (M+H)+.

What is claimed is:

1. N-(4-chlorobenzyl)-8-(3-hydroxy-1-propynyl)-1-methyl-6-(4-morpholinylmethyl)-4-oxo-1,4-dihydro-3-quinolinecarboxamide, or its pharmaceutically acceptable salt thereof.

2. A pharmaceutical composition comprising a therapeutically effective amount of compound of claim 1 and a pharmaceutically acceptable carrier.

3. A method of treating infections by herpesviruses, wherein said herpesviruses is herpes simplex virus types 1, herpes simplex virus types 2, varicella zoster virus, cytomegalovirus, Epstein-Barr virus, human herpes viruses 6, human herpes viruses 7 or human herpes viruses, which comprises administering to an animal in need thereof a therapeutically effective amount of compound of claim 1.

4. The method of claim 3 wherein said herpesviruses is human cytomegalovirus.

5. The method of claim 3 wherein the compound of claim 1 is administered orally, parenterally or topically.

6. The method of claim 3 wherein the compound of claim 1 is in an amount of from about 0.1 to about 300 mg/kg of body weight.

7. The method of claim 3, wherein the compound of claim 1 is in an amount of from about 1 to about 30 mg/kg of body weight.

8. The method of claim 3, wherein the animal is mammal.

9. The method of claim 3, wherein the animal is human.

* * * * *